(12) United States Patent
Hubalek et al.

(10) Patent No.: US 11,498,951 B2
(45) Date of Patent: Nov. 15, 2022

(54) INSULIN ANALOGUES AND USES THEREOF

(71) Applicant: Novo Nordisk A/S, Bagsvaerd (DK)

(72) Inventors: Frantisek Hubalek, Herlev (DK); Mathias Norrman, Staffanstorp (SE); Helle Birk Olsen, Alleroed (DK); Peter Madsen, Bagsvaerd (DK); Thomas Boerglum Kjeldsen, Virum (DK); Jeppe Sturis, Vaerloese (DK)

(73) Assignee: Novo Nordisk A/S, Bagsvaerd (DK)

( * ) Notice: Subject to any disclaimer, the term of this patent is extended or adjusted under 35 U.S.C. 154(b) by 0 days.

(21) Appl. No.: 17/117,263

(22) Filed: Dec. 10, 2020

(65) Prior Publication Data

US 2021/0179685 A1 Jun. 17, 2021

(30) Foreign Application Priority Data

Dec. 11, 2019 (EP) .................... 19215315

(51) Int. Cl.
*C07K 14/62* (2006.01)
*A61P 3/10* (2006.01)
*A61K 47/22* (2006.01)

(52) U.S. Cl.
CPC .............. *C07K 14/62* (2013.01); *A61K 47/22* (2013.01); *A61P 3/10* (2018.01)

(58) Field of Classification Search
None
See application file for complete search history.

(56) References Cited

U.S. PATENT DOCUMENTS

| | | | |
|---|---|---|---|
| 5,382,574 A | 1/1995 | Jorgensen | |
| 5,618,913 A * | 4/1997 | Brange | C07K 14/62 530/303 |
| 5,750,497 A | 5/1998 | Havelund et al. | |
| 5,922,678 A | 7/1999 | Stephens | |
| 6,960,561 B2 | 11/2005 | Boderke | |
| 9,068,013 B2 | 6/2015 | Lancaster et al. | |
| 2001/0036916 A1 | 11/2001 | Brader | |
| 2005/0085621 A1 | 4/2005 | Berchtold | |
| 2007/0129284 A1 | 6/2007 | Kjeldsen et al. | |
| 2014/0315797 A1 | 10/2014 | Madsen et al. | |

FOREIGN PATENT DOCUMENTS

| | | | |
|---|---|---|---|
| CN | 105440125 A | 3/2016 | |
| EP | 2784085 A1 | 10/2014 | |
| JP | 2001521006 A | 11/2001 | |
| JP | 2008502313 A | 1/2008 | |
| JP | 2010535841 A | 11/2010 | |
| JP | 2013541500 A | 11/2013 | |
| WO | 98/42749 A1 | 10/1998 | |
| WO | 06097521 A1 | 9/2006 | |
| WO | 07096431 A1 | 8/2007 | |
| WO | 2007096431 A1 | 8/2007 | |
| WO | 2007104738 A2 | 9/2007 | |
| WO | 2009011005 A1 | 1/2009 | |
| WO | 09/022006 A1 | 2/2009 | |
| WO | 2009022005 A1 | 2/2009 | |
| WO | 09022005 A1 | 2/2009 | |
| WO | 2009021955 | 2/2009 | |
| WO | 2009022013 A1 | 2/2009 | |
| WO | 2009/112583 A2 | 9/2009 | |
| WO | 2009115469 A1 | 9/2009 | |
| WO | 09121884 A1 | 10/2009 | |
| WO | 2011/000823 A1 | 1/2011 | |
| WO | 2011051486 A2 | 5/2011 | |
| WO | 2011161124 A1 | 12/2011 | |
| WO | 2012/171994 A1 | 12/2012 | |
| WO | 2013/063572 A1 | 5/2013 | |
| WO | 14158900 A1 | 10/2014 | |
| WO | 15051052 A2 | 4/2015 | |
| WO | 2015/128403 A2 | 9/2015 | |
| WO | 2017032795 A1 | 3/2017 | |
| WO | 2017032798 A1 | 3/2017 | |
| WO | WO-2017032795 A1 * | 3/2017 | ................ A61P 3/10 |
| WO | 19125879 | 6/2019 | |

OTHER PUBLICATIONS

Brange et al. "Chemical stability of insulin. 4. Mechanisms and kinetics of chemical transformations in pharmaceutical formulation." Acta Pharmaceutica Nordica 1992 vol. 4(4) pp. 209-222.
Brange, J et al. "Chemical Stability of Insulin 3. Influence of Excipients, formulation and pH." Acta Pharma Nordica 1992 vol. 4(3) pp. 149-158.
Hahr, A J et al. "Optimizing insulin therapy in patients with type 1 and type 2 diabetes mellitus: optimal dosing and timing in the outpatient setting." Disease-a-month 2010 vol. 56(3) pp. 148-162.
Huus K et al. "Chemical and thermal stability of insulin: effects of zinc and ligand binding to the insulin zinc-hexamer" Pharmaceutical Research 2006 vol. 23(11) pp. 2611-2620.
Encyclopedia Britannica (https://www.britannica.com/science/metabolic-disease); accessed Mar. 18, 2019.
The Merck Manual (https://www.merckmanuals.com/professional/pediatrics/inherited-disorders-of-metabolism/urea-cycle-disorders?query=urea%20defects, copyright 2018); accessed Aug. 30, 2019.
The Merck Manual (https://www.merckmanuals.com/professional/pediatrics/inherited-disorders-of-metabolism/phenylketonuria-pku, copyright 2018); accessed Aug. 30, 2019.

(Continued)

*Primary Examiner* — Sudhakar Katakam
*Assistant Examiner* — Zachary J Miknis
(74) *Attorney, Agent, or Firm* — Rosemarie R. Wilk-Orescan

(57) ABSTRACT

The present invention is in the therapeutic field of drugs for medical conditions relating to diabetes. More specifically the invention relates to insulin analogues of human insulin. The invention provides pharmaceutical compositions comprising such insulin analogues and the uses if the such analogues for the treatment or prevention of medical conditions relating to diabetes.

15 Claims, 2 Drawing Sheets

Specification includes a Sequence Listing.

(56) References Cited

OTHER PUBLICATIONS

Epstein, Charles J., "Non-randomness of Amino-acid changes in teh evolution of homologous proteins." Nature, 1967, vol. 215, No. 5099, Tables 1-2, pp. 355-359.

Forbes et al., "Mechanisms of diabetic complications." Physiological reviews, 2013, vol. 93, No. 1, pp. 137-188.

Haberle et al., "Suggested guidelines for the diagnosis and management of urea cycle disorders." Orghanet J. Rare Dis. 2012, vol. 7, No. 32, pp. 1-30.

Yao, Z-P., et al. "Structure of an insulin dimer in an orthorhombic crystal: the structure analysis of a human insulin mutant (B9 Ser? Glu)." Acta Crystallographica Section D: Biological Crystallography, Sep. 1999, vol. 55, No. 9, pp. 1524-1532.

Zoete et al.. "A comparison of the dynamic behavior of monomeric and dimeric insulin shows structural rearrangements in the active monomer." Journal of molecular biology, Sep. 2004, vol. 342, No. 3, pp. 913-929.

Brange et al. "Monomeric insulins and their experimental and clinical implications." Diabetes Care, Sep. 1990, vol. 13, No. 9, pp. 923-954.

Dimarchi et al. "Three chain insulin analogs demonsliate the importance of insulin secondary structure to bioactivity." Journal of Peptide Science, Mar. 2015, vol. 21, No. 3, pp. 223-230.

Hjorth et al., "Purification and identification of high molecular weight products formed during storage of neutral formulation of human insulin," Pharm. Res., 2015, vol. 32, No. 6, pp. 2072-2085.

Hjorth et al., "Structure, Aggregation, and Activity of a Covalent Insulin Dimer Formed During Storage of Neutral Formulation of Human Insulin," J. Pharm. Sci., 2016, vol. 105, No. 4, pp. 1376-1386.

Min et al., "Insulin related compounds and identification," J. Chromatogr. B, 2012, vol. 908, pp. 105-112.

\* cited by examiner ately filed Dec. 11, 2019; the contents of
INSULIN ANALOGUES AND USES THEREOF

CROSS-REFERENCE TO RELATED APPLICATIONS

This application claims priority to European Patent Application 19215315.3, filed Dec. 11, 2019; the contents of which are incorporated herein by reference.

SEQUENCE LISTING

The instant application contains a Sequence Listing which has been submitted in ASCII format via EFS-Web and is hereby incorporated by reference in its entirety. Said ASCII copy, created on Dec. 4, 2020, is named 190084US01_SeqList.txt and is 4 kilobytes in size.

TECHNICAL FIELD

The present invention relates to novel analogues of human insulin, pharmaceutical compositions comprising such insulin analogues and the use of such analogues for the treatment or prevention of medical conditions relating to diabetes.

BACKGROUND

Insulin therapy for the treatment of diabetes has been used for decades. One of the key improvements in insulin therapy has been the introduction of rapid-acting insulin analogues.

Insulin possesses self-association properties, and its concentration represents a major factor of self-association. At high concentrations, especially in pharmaceutical compositions, insulin will self-associate into dimer, hexamer, dodecamer or higher molecular structures. However, the physiologically active form of insulin is the monomer, which binds with the insulin receptor and triggers a biological response. It is a challenge to reduce self-association of insulin analogues, particularly at high concentration in a pharmaceutical composition.

The rapidity of insulin action is dependent on how quickly the insulin is absorbed from the subcutaneous tissue. In general, when a commercially available insulin composition is injected subcutaneously, the composition is primarily composed of hexamers containing two zinc ions. Although these two zinc ions located within the hexamer stabilize the molecule towards chemical and physical degradation in a composition, due to its size, the hexameric insulin has a lower rate of diffusion and consequently, the absorption rate is slower than for smaller species.

WO2017/032795 and WO2017/032798 relate to acylated insulin analogues in low zinc or zinc free composition.

Zinc-free insulin compositions enable faster subcutaneous absorption, but chemical and physical stability of zinc-free compositions is a challenge, particularly at high concentrations.

There is a strong need for insulin analogues that are rapid acting, while at the same time being sufficiently physically and chemically stable at high concentrations in a zinc free composition.

SUMMARY

In the broadest aspect, the present invention relates to rapid acting analogues of human insulin.

In one aspect, the present invention relates to analogues of human insulin comprising amino acid modification at position A9 and further comprising up to 5 to 10 amino acid modifications relative to human insulin.

In one aspect, the present invention relates to analogues of human insulin, wherein the analogue comprises A9Glu or A9Asp and further comprises B3Glu and/or desB30 relative to human insulin.

In one aspect, the present invention relates to analogues of human insulin, wherein the analogue comprises A9Glu or A9Asp and further comprises B3Glu and/or desB30 relative to human insulin and/or further comprises at least one of B26Glu, B27Glu and/or B28Glu.

In one aspect, the present invention relates to analogues of human insulin, wherein the analogue comprises A9Glu or A9Asp and further comprises B3Glu and/or desB30 relative to human insulin and/or further comprises at least one of B26Glu, B27Glu and/or B28Glu and additionally comprises A21Ala substitution.

In one aspect, the present invention provides insulin analogues that are monomeric in a zinc free pharmaceutical composition.

In one aspect, the present invention provides insulin analogues are physically and/or chemically stable in a zinc free pharmaceutical composition.

In another aspect, the insulin analogues of the present invention are monomeric, chemically and physically stable, even at a high concentration, in a zinc free pharmaceutical composition.

In one aspect, the present invention provides Insulin analogues that are absorbed more rapidly after subcutaneous administration, thereby demonstrating a potential clinical utility as rapid acting insulins (also called bolus or prandial insulins).

In one aspect, the present invention relates to a zinc free pharmaceutical composition comprising the insulin analogues of the invention and one or more pharmaceutically acceptable excipients.

In further aspect, the insulin analogues of the present invention are compatible with insulin delivery system.

In further aspect, the insulin analogues of the present invention are compatible with a closed loop insulin delivery system.

In further aspect, the insulin analogues of the present invention are suitable for use in insulin pumps.

The invention may also solve further problems that will be apparent from the disclosure of the exemplary embodiments.

DESCRIPTION

Figure 1:
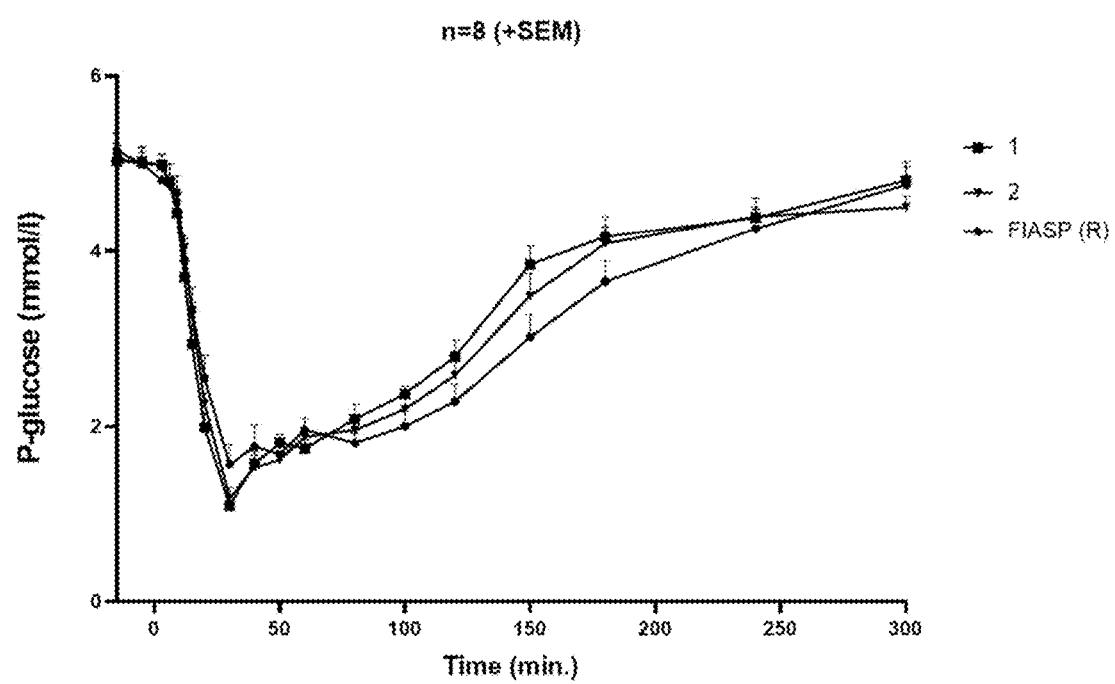
FIG. 1 shows PD profile of insulin analogues of example 1 and example 2 in pharmaceutical composition C of the invention after dosing LYD pigs as compared to Fiasp® (Insulin Aspart)

The present invention relates to rapid acting insulin analogues that are monomeric, provide acceptable chemical and physical stability in a zinc free pharmaceutical composition and faster absorption after subcutaneous administration than commercially available Fiasp® (Insulin Aspart).

Definitions

Unless otherwise indicated in the specification, terms presented in singular form also include the plural situation.

The terms "invention" and "present invention" are used interchangeably.

The term "about" is used herein intended to mean plus or minus 10%, such as plus or minus 5%. Hence, the term "about 100 U" is from 90 U to 110 U.

Following table provides concentration of human insulin in mM and corresponding concentration in (U) equivalent to human insulin:

| Concentration of Insulin analogue (in mM) | Concentration of insulin analogue in (U) equivalent to human insulin |
|---|---|
| 0.6 | 100 U |
| 1.2 | 200 U |
| 1.8 | 300 U |
| 2.4 | 400 U |
| 3.0 | 500 U |
| 3.6 | 600 U |

The term "amino acid" includes proteinogenic (or natural) amino acids (amongst those the 20 standard amino acids), as well as non-proteinogenic (or non-natural) amino acids. Proteinogenic amino acids are those which are naturally incorporated into proteins. The standard amino acids are those encoded by the genetic code. Non-proteinogenic amino acids are either not found in proteins, or not produced by standard cellular machinery (e.g., they may have been subject to post-translational modification).

In general, amino acid residues (peptide/protein sequences) as used herein, may be identified by their full name, their one-letter code, and/or their three-letter code. These three ways are fully equivalent and interchangeable. For example: Aspartic acid is represented by Asp or D; Glutamic acid is represented by Glu or E; Alanine is represented by Ala or A.

In what follows, each amino acid of the peptides of the invention for which the optical isomer is not stated is to be understood to mean the L-isomer (unless otherwise specified). Amino acids are molecules containing an amino group and a carboxylic acid group, and, optionally, one or more additional groups, often referred to as a side chain. Herein, the term "amino acid residue" is an amino acid from which, formally, a hydroxy group has been removed from a carboxy group and/or from which, formally, a hydrogen atom has been removed from an amino group.

The term "compound" is used herein to refer to a molecular entity, and "compounds" may thus have different structural elements besides the minimum element defined for each compound or group of compounds. The term "compound" is also meant to cover pharmaceutically relevant forms hereof, i.e. the invention relates to a compound as defined herein or a pharmaceutically acceptable salt, amide, or ester thereof.

The term "human Insulin" as used herein means the human insulin hormone whose structure and properties are well-known. Human insulin has two polypeptide chains, named the A-chain and the B-chain. The A-chain is a 21 amino acid peptide and the B-chain is a 30 amino acid peptide, the two chains being connected by disulphide bridges: a first bridge between the cysteine in position 7 of the A-chain and the cysteine in position 7 of the B-chain, and a second bridge between the cysteine in position 20 of the A-chain and the cysteine in position 19 of the B-chain. A third bridge is present between the cysteines in position 6 and 11 of the A-chain.

The human insulin A-chain has the following sequence:

(SEQ ID NO: 1)
GIVEQCCTSICSLYQLENYCN, while the B-chain has the following sequence:

(SEQ ID NO: 2)
FVNQHLCGSHLVEALYLVCGERGFFYTPKT.

In the human body, the hormone is synthesized as a single-chain precursor proinsulin (preproinsulin) consisting of a prepeptide of 24 amino acids followed by proinsulin containing 86 amino acids in the configuration: prepeptide-B-Arg Arg-C-Lys Arg-A, in which C is a connecting peptide of 31 amino acids. Arg-Arg and Lys-Arg are cleavage sites for cleavage of the connecting peptide from the A and B chains.

"An Insulin" according to the invention is herein to be understood as human insulin or an insulin from another species such as porcine or bovine insulin.

"Rapid-acting Insulin" as used herein means insulin analogues according to the invention that begin to work about 15 minutes after injection, peaks in about 1 hour, and continues to work for 2 to 4 hours. Types: Insulin glulisine (Apidra), insulin lispro (Admelog, Humalog), and insulin aspart (Fiasp, NovoLog).

The term "Insulin peptide", "Insulin compound" or "Insulin" as used herein means a peptide which is either human insulin or an analogue thereof with insulin activity, i.e., which activates the insulin receptor.

Nomenclature

Naming of the insulin analogues of the present invention is done according to the following principles:

For example, the insulin analogue B3E, B27E, B28E, desB30 human insulin indicates that the amino acid in position B3, Asparagine (N) has been substituted with glutamic acid (E), the amino acid in position B27, Threonine (T) in human insulin, has been substituted with glutamic acid (E), the amino acid in position B28, Proline (P) in human insulin, has been substituted with glutamic acid (E) and the amino acid in position B30, Threonine, T, in human insulin, has been deleted.

Insulin Analogue

The term "Insulin analogue" as used herein means the modified human insulin wherein one or more amino acid residues of the insulin have been substituted by other amino acid residues and/or wherein one or more amino acid residues have been deleted from the insulin and/or wherein one or more amino acid residues have been added and/or inserted to the insulin. The terms "insulin analogue" or "analogue of human insulin" are used interchangeably.

The term "amino acid modification" as used herein means substitution, deletion, addition or insertion of amino acid and any combination thereof relative to human insulin.

Modifications in the insulin molecule are denoted stating the chain (A or B), the position, and the one or three letter code for the amino acid residue substituting the native amino acid residue.

In one embodiment an insulin analogue comprises up to 10 amino acid modifications (substitutions, deletions, additions (including insertions) and any combination thereof) relative to human insulin, alternatively up to 9, 8, 7, 6, 5, 4, 3, 2 or 1 modification relative to human insulin.

Analogues "comprising" certain specified changes may comprise further changes, when compared to human insulin chain A (SEQ ID NO: 1) and/or chain B (SEQ ID NO:2).

By "connecting peptide" or "C-peptide" is meant a connection moiety "C" of the B-C-A polypeptide sequence of a single chain proinsulin-molecule. In the human insulin chain, the C-peptide connects position 30 of the B chain and position 1 of the A chain and is 35 amino acid residue long. The connecting peptide includes two terminal dibasic amino acid sequence, e.g., Arg-Arg and Lys-Arg which serve as cleavage sites for cleavage off of the connecting peptide from the A and B chains to form the two-chain insulin molecule.

By "desB30" or "B(1-29)" is meant a natural insulin B chain or an analogue thereof lacking the B30 amino acid and "A(1-21)" means the natural insulin A chain. Thus, e.g., desB30 human insulin is an analogue of human insulin where the amino acid in position 30 in the B chain is deleted.

The term "peptide" or "polypeptide", as e.g. used in the context of the invention, refers to a compound which comprises a series of amino acids interconnected by amide (or peptide) bonds. In a particular embodiment the peptide consists of amino acids interconnected by peptide bonds.

The term "chemical stability" of the protein preparation as used herein refers to changes in the covalent protein structure leading to formation of chemical degradation products with potential less biological potency and/or potential increased immunogenic properties compared to the native protein structure. Various chemical degradation products can be formed depending on the type and nature of the native protein and the environment to which the protein is exposed. Increasing amounts of chemical degradation products are often seen during storage and use of the protein preparation. Most proteins are prone to deamidation, a process in which the side chain amide group in glutaminyl or asparaginyl residues is hydrolysed to form a free carboxylic acid or asparaginyl residues to form an isoAsp derivative. Other degradation pathways involve formation of High Molecular Weight Products (HMWP) where two or more protein molecules are covalently bound to each other through, for example transamidation and/or disulfide interactions leading to formation of covalently bound dimer, oligomer and polymer degradation products (Stability of Protein Pharmaceuticals, Ahern T J & Manning M G, Plenum Press, New York 1992). Oxidation can be mentioned as another variant of chemical degradation. The chemical stability of the protein preparation can be evaluated by measuring the amount of the chemical degradation products at various time-points after exposure to different environmental conditions (the formation of degradation products can often be accelerated by for instance increasing temperature). The amount of each individual degradation product is often determined by separation of the degradation products depending on molecule size, hydrofobicity, and/or charge using various chromatography techniques (e.g. SEC-HPLC and/or RP-HPLC). Since HMWP products are potentially immunogenic and not biologically active, low levels of HMWP are advantageous.

The term "physical stability" of the insulin preparation as used herein refers to the tendency of the protein to form biologically inactive and/or insoluble aggregates of the protein as a result of exposure of the protein to thermomechanical stresses and/or interaction with interfaces and surfaces that are destabilizing, such as hydrophobic surfaces and interfaces. Physical stability of the aqueous protein preparations is evaluated by means of visual inspection and/or turbidity measurements after exposing the preparation filled in suitable containers (e.g. cartridges or vials) to mechanical/physical stress (e.g. agitation) at different temperatures for various time periods. Visual inspection of the preparations is performed in a sharp focused light with a dark background. A preparation is classified physically unstable with respect to protein aggregation, when it shows visual turbidity in daylight. Alternatively, the turbidity of the preparation can be evaluated by simple turbidity measurements well-known to the skilled person. Physical stability of the aqueous protein preparations can also be evaluated by using a spectroscopic agent or probe of the conformational status of the protein. The probe is preferably a small molecule that preferentially binds to a non-native conformer of the protein. One example of a small molecular spectroscopic probe of protein structure is Thioflavin T. Thioflavin T is a fluorescent dye that has been widely used for the detection of amyloid fibrils. In the presence of fibrils, and perhaps other protein configurations as well, Thioflavin T gives rise to a new excitation maximum at about 450 nm and enhanced emission at about 482 nm when bound to a fibril protein form. Unbound Thioflavin T is essentially non-fluorescent at the wavelengths.

The term "high concentration" of the insulin preparation as used herein refers to the concentration of insulin that is 200 U or above; 1.2 mM or above.

In one embodiment, the present invention relates to analogues of human insulin comprising amino acid modification at position A9 and further comprising 1 to 10 amino acid modifications relative to human insulin.

In one embodiment, the present invention relates to insulin analogues comprising amino acid modification at position A9 relative to human insulin and further comprising amino acid modification at position B3 and/or desB30 relative to human insulin.

In one embodiment, the present invention relates to analogues of human insulin, wherein the analogue comprises A9Glu or A9Asp.

In one embodiment, the present invention relates to analogues of human insulin wherein the analogue comprises A9Glu or A9Asp and further comprising 1 to 10 amino acid modifications relative to human insulin.

In one embodiment, the present invention relates to insulin analogues comprising A9Glu or A9Asp relative to human insulin and further comprising amino acid modification at position B3 and/or desB30 relative to human insulin.

In one embodiment, the present invention relates to analogues of human insulin, wherein the analogue comprises A9Glu or A9Asp and further comprises B3Glu and/or desB30 relative to human insulin.

In one embodiment, the present invention relates to analogues of human insulin, wherein the analogue comprises A9Glu or A9Asp or A9Gln and further comprises B3Glu or B3Gln and/or desB30 relative to human insulin.

The present invention relates to analogues of human insulin, wherein the analogue comprises A9Glu or A9Asp and further comprises B3Glu and/or desB30 relative to human insulin and further comprising 5 to 10 amino acid modifications relative to human insulin.

The present invention relates to analogues of human insulin, wherein the analogue comprises A9Glu or A9Asp and further comprises B3Glu and/or desB30 relative to human insulin and further comprising up to 10 amino acid modifications relative to human insulin.

The present invention relates to analogues of human insulin, wherein the analogue comprises A9Glu or A9Asp and further comprises B3Glu and/or desB30 relative to human insulin and further comprising up to 8 amino acid modifications relative to human insulin.

The present invention relates to analogues of human insulin, wherein the analogue comprises A9Glu or A9Asp and further comprises B3Glu and/or desB30 relative to human insulin and further comprising up to 6 amino acid modifications relative to human insulin.

The present invention relates to analogues of human insulin, wherein the analogue comprises A9Glu or A9Asp and further comprises B3Glu and/or desB30 relative to human insulin and further comprising up to 4 amino acid modifications relative to human insulin.

The present invention relates to analogues of human insulin, wherein the analogue comprises A9Glu or A9Asp and further comprises B3Glu and/or desB30 relative to human insulin and further comprising up to 3 amino acid modifications relative to human insulin.

The present invention relates to analogues of human insulin, wherein the analogue comprises A9Glu or A9Asp and further comprises B3Glu and/or desB30 relative to human insulin and further comprising up to 2 amino acid modifications relative to human insulin.

In one aspect, the present invention relates to analogues of human insulin, wherein the analogue comprises A9Glu or A9Asp and further comprises B3Glu and/or desB30 relative to human insulin and further comprises at least one of B26Glu, B27Glu and/or B28Glu.

In one aspect, the present invention relates to analogues of human insulin, wherein the analogue comprises A9Glu or A9Asp or A9Gln and further comprises B3Glu or B3Gln and/or desB30 relative to human insulin and further comprises at least one of B26Glu, B27Glu and/or B28Glu.

In one aspect, the present invention relates to analogues of human insulin, wherein the analogue comprises A9Glu or A9Asp and further comprises B3Glu and/or desB30 relative to human insulin and/or further comprises at least one of B26Glu, B27Glu and/or B28Glu and additionally comprises A21A substitution.

In one aspect, the present invention relates to analogues of human insulin, wherein the analogue comprises A9Glu or A9Asp or A9Gln and further comprises B3Glu or B3Gln and/or desB30 relative to human insulin and/or further comprises at least one of B26Glu, B27Glu and/or B28Glu and additionally comprises A21A substitution.

Pharmaceutical Indications

Diabetes

The term "diabetes" or "diabetes mellitus" includes type 1 diabetes, type 2 diabetes, gestational diabetes (during pregnancy) and other states that cause hyperglycaemia. The term is used for a metabolic disorder in which the pancreas produces insufficient amounts of insulin, or in which the cells of the body fail to respond appropriately to insulin thus preventing cells from absorbing glucose. As a result, glucose builds up in the blood.

Type 1 diabetes, also called insulin-dependent diabetes mellitus (IDDM) and juvenile-onset diabetes, is caused by B-cell destruction, usually leading to absolute insulin deficiency.

Type 2 diabetes, also known as non-insulin-dependent diabetes mellitus (NIDDM) and adult-onset diabetes, is associated with predominant insulin resistance and thus relative insulin deficiency and/or a predominantly insulin secretory defect with insulin resistance.

Methods of Synthesis

The insulin analogues of the invention may be obtained by conventional methods for the preparation of insulin analogues, and in particular the methods described in the working examples.

Biological Activity

The insulin analogues of the invention are rapid acting.

The insulin analogues of the invention all possess insulin receptor affinities adequate for activating the insulin receptor in order to give the glycaemic response needed, i.e. being able to lower blood glucose in animals and humans. As a measure of functional (agonistic) activity of the insulins of the invention, lipogenesis activity in rat adipocytes are demonstrated.

The insulin analogues of the invention are found to have a balanced insulin receptor (IR) to insulin-like growth factor 1 receptor (IGF-1R) affinity ratio (IR/IGF-1R).

In one aspect, the insulin of the invention has an IR/IGF-1R ratio of above 1; of above 1.5; or of above 2.

In one embodiment, the analogue of human insulin of the invention has the ability to reduce blood glucose levels.

In one embodiment, the analogue of human insulin of the invention activates the insulin receptor.

In one embodiment, the analogue of human insulin of the invention lowers blood glucose.

In one embodiment, the analogue of human insulin of the invention has reduced self-association properties.

In one embodiment, the analogue of human insulin of the invention is monomeric.

In one aspect the invention provides novel insulin analogues for use as medicaments, or for use in the manufacture of medicaments or pharmaceutical compositions. The insulin analogue of the invention may in particular be useful as medicaments for the treatment of metabolic disorders including diabetes, particularly Type 1 diabetes and Type 2 diabetes.

Pharmaceutical Compositions

The present invention relates to insulin analogues useful as medicaments, or for the manufacture of a pharmaceutical composition/medicament.

Therefore, in another aspect, the invention provides novel pharmaceutical compositions comprising a therapeutically effective amount of an insulin analogue according to the present invention.

The pharmaceutical composition according to the invention optionally comprises one or more pharmaceutically acceptable excipients.

The pharmaceutical composition of the present invention may further comprise other excipients commonly used in pharmaceutical compositions e.g. preservatives, chelating agents, tonicity agents, absorption enhancers.

In one embodiment of the invention the pharmaceutical composition of the invention is an aqueous preparation, i.e. preparation comprising water. Such preparation is typically a solution. In a further embodiment of the invention the pharmaceutical composition is an aqueous solution.

The term "aqueous preparation" is defined as a preparation comprising at least 50% w/w water. Likewise, the term "aqueous solution" is defined as a solution comprising at least 50% w/w water.

In one embodiment of the invention the insulin preparation comprises an aqueous solution of an insulin analogue of the present invention, wherein said insulin analogue is present in a concentration of about 0.1 mM to about 20.0 mM; more particularly of from about 0.2 mM to about 6.0 mM; of from about 0.3 mM to about 4.0 mM; of from about 0.6 mM to about 3.6 mM. In one embodiment, the insulin analogue of the present invention is in a concentration of from about 0.6 mM to about 3.0 mM. In one embodiment, the insulin analogue of the present invention is in a concentration of about 0.6 mM. In one embodiment, the insulin analogue of the present invention is in a concentration of about 1.2 mM. In one embodiment, the insulin analogue of the present invention is in a concentration of about 1.8 mM.

In one embodiment, the insulin analogue of the present invention is in a concentration of about 2.4 mM. In one embodiment, the insulin analogue of the present invention is in a concentration of about 3 mM. In one embodiment, the insulin analogue of the present invention is in a concentration of about 3.6 mM.

In one embodiment, the insulin analogue of the present invention is in a concentration of from about 100 U to about 600 U. In one embodiment, the insulin analogue of the present invention is in a concentration of about 100 U. In one embodiment, the insulin analogue of the present invention is in a concentration of about 200 U. In one embodiment, the insulin analogue of the present invention is in a concentration of about 300 U. In one embodiment, the insulin analogue of the present invention is in a concentration of about 400 U. In one embodiment, the insulin analogue of the present invention is in a concentration of about 500 U. In one embodiment, the insulin analogue of the present invention is in a concentration of about 600 U.

The pharmaceutical composition of the present invention may further comprise a buffer system. In one embodiment, the concentration of buffer is in the range from about 0.1 mM to 20 mM. In yet another embodiment the concentration of said buffer is in the range from 0.1 mM to about 10 mM, or from about 0.1 mM to about 8 mM, from about 1 mM to about 8 mM, or from about 2 mM to about 8 mM, or from 3 mM to 7 mM. In one embodiment of the invention the buffer is a phosphate buffer. In one embodiment of the present invention, the concentration of the phosphate buffer is 3 mM. In one embodiment of the invention the buffer is Tris. In one embodiment of the present invention, the concentration of the Tris buffer is 7 mM.

In one embodiment, the pharmaceutical composition of the present invention may not comprise a buffer.

The pH of the injectable pharmaceutical composition of the invention is in the range of from 3 to 8.5. Preferably, the injectable pharmaceutical composition according to the invention has a pH in the range from about 7.0 to about 8.0. In one embodiment of the invention the pH is in the range from about 7.2 to about 7.8, or from 7.4 to 7.6. In one embodiment of the invention, the pH is 7.0. In one embodiment of the invention, the pH is 7.2. In one embodiment of the invention, the pH is 7.4. In one embodiment of the invention, the pH is 7.6. In one embodiment of the invention, the pH is 7.8. In one embodiment of the invention, the pH is 8.0.

The insulin preparations of the present invention may further comprise a tonicity agent.

In one embodiment of the invention, tonicity agent is glycerol and/or propylene glycol and/or sodium chloride may be present in a concentration of from 0 to about 250 mM, from 0 to about 200 mM, or from 0 to about 100 mM. In one embodiment, tonicity agent may be present in a concentration of about 230 mM. In one embodiment, tonicity agent may be present in a concentration of 233 mM. In one embodiment, tonicity agent may be present in a concentration of 230 mM. In one embodiment, tonicity agent may be present in a concentration of about 200 mM. In one embodiment, tonicity agent may be present in a concentration of 200 mM. In one embodiment, tonicity agent may be present in a concentration of about 195 mM. In one embodiment, tonicity agent may be present in a concentration of 195 mM. In one embodiment, tonicity agent may be present in a concentration of about 185 mM. In one embodiment, tonicity agent may be present in a concentration of 185 mM. In one embodiment, tonicity agent may be present in a concentration of about 165 mM. In one embodiment, tonicity agent may be present in a concentration of 163 mM. In one embodiment, tonicity agent may be present in a concentration of 130 mM. In one embodiment, tonicity agent may be present in a concentration of about 100 mM. In one embodiment, tonicity agent may be present in a concentration of 103 mM.

The insulin preparations of the present invention may further comprise a pharmaceutically acceptable preservative. The preservative may be present in an amount sufficient to obtain a preserving effect. The amount of preservative in a pharmaceutical composition of the invention may be determined from e.g. literature in the field and/or the known amount(s) of preservative in e.g. commercial products. Each one of these specific preservatives or mixtures hereof constitutes an alternative embodiment of the invention. The use of a preservative in pharmaceutical preparations is described, for example in Remington: The Science and Practice of Pharmacy, 19th edition, 1995.

In one embodiment of the invention, the injectable pharmaceutical composition comprises at least one phenolic compound as preservative agent. In one embodiment the phenolic compound for use according to the invention may be present in up to about 6 mg/mL of final injectable pharmaceutical composition, in particular of up to about 4 mg/mL of final injectable pharmaceutical composition. In one embodiment the phenolic compound for use according to the invention may be present in an amount of up to about 4.0 mg/mL of final injectable pharmaceutical composition; in particular of from about 0.5 mg/mL to about 4.0 mg/mL; or of from about 0.6 mg/mL to about 4.0 mg/ml. In one embodiment of the invention the preservative is phenol. In one embodiment of the invention, the injectable pharmaceutical composition comprises a mixture of phenol and m-cresol as preservative agent. In one embodiment of the invention, the injectable pharmaceutical composition comprises about 16 mM phenol (1.5 mg/ml) and about 16 mM m-cresol (1.72 mg/ml). In one embodiment of the invention, the injectable pharmaceutical composition comprises about 19 mM phenol (1.79 mg/ml) and about 19 mM m-cresol (2.05 mg/ml).

The pharmaceutical composition of the present invention may further comprise a chelating agent. In one aspect, the pharmaceutical composition of the present invention may not comprise a chelating agent. The use of a chelating agent in pharmaceutical preparations is well-known to the skilled person. For convenience reference is made to Remington: The Science and Practice of Pharmacy, 19th edition, 1995.

The pharmaceutical composition of the present invention may further comprise a absorption enhancer. The group of absorption enhancers may include but is not limited to nicotinic compounds.

In one embodiment of the invention, the pharmaceutical composition comprises of a nicotinic compound. In one embodiment the nicotinic compound is nicotinamide, and/or nicotinic acid, and/or a salt thereof. In another embodiment the nicotinic compound is nicotinamide. In another embodiment of the invention, the nicotinic compound is present in the amount of from about 0 mM to about 200 mM; in particular in the amount of from about 10 mM to about 200 mM such as about 10 mM, about 20 mM, about 40 mM, about 170 mM.

In one embodiment, the pharmaceutical composition of the present invention does not comprise of a nicotinic compound.

In one embodiment of the invention, the pharmaceutical composition comprises citrate in a concentration from 1 mM to 50 mM. The term citrate is to be understood to include citrate sat as well as citric acid. In one embodiment of the invention, the pharmaceutical composition comprises citrate in a concentration from 5 mM to 20 mM. In one embodiment of the invention, citrate is present in a concentration of 5 mM. In one embodiment of the invention, citrate is present in a concentration of 10 mM. In one embodiment of the invention, citrate is present in a concentration of 15 mM. In one embodiment of the invention, citrate is present in a concentration of 20 mM.

In one embodiment of the invention, the pharmaceutical composition comprises nicotinamide and citrate. In one embodiment of the invention, the pharmaceutical composition comprises a combination of nicotinamide and citrate, where nicotinamide is present in the amount of from about 5 mM to about 200 mM, in particular in the amount of from about 20 mM to about 200 mM such as about 10 mM, about 20 mM, about 40 mM, about 170 mM and citrate is present in a concentration range of 5 mM to 20 mM, in particular in a concentration of about 5 mM, about 10 mM, about 15 mM, about 20 mM. In one embodiment of the invention, the pharmaceutical composition comprises 5 mM nicotinamide and 5 mM citrate. In one embodiment of the invention, the pharmaceutical composition comprises 10 mM nicotinamide and 5 mM citrate. In one embodiment of the invention, the pharmaceutical composition comprises 20 mM nicotinamide and 5 mM citrate. In one embodiment of the invention, the pharmaceutical composition comprises 40 mM nicotinamide and 5 mM citrate. In one embodiment of the invention, the pharmaceutical composition comprises 60 mM nicotinamide and 5 mM citrate. In one embodiment of the invention, the pharmaceutical composition comprises 80 mM nicotinamide and 5 mM citrate. In one embodiment of the invention, the pharmaceutical composition comprises 100 mM nicotinamide and 5 mM citrate. In one embodiment of the invention, the pharmaceutical composition comprises 120 mM nicotinamide and 5 mM citrate. In one embodiment of the invention, the pharmaceutical composition comprises 140 mM nicotinamide and 5 mM citrate. In one embodiment of the invention, the pharmaceutical composition comprises 160 mM nicotinamide and 5 mM citrate. In one embodiment of the invention, the pharmaceutical composition comprises 170 mM nicotinamide and 5 mM citrate. In one embodiment of the invention, the pharmaceutical composition comprises 5 mM nicotinamide and 10 mM citrate. In one embodiment of the invention, the pharmaceutical composition comprises 10 mM nicotinamide and 10 mM citrate. In one embodiment of the invention, the pharmaceutical composition comprises 20 mM nicotinamide and 10 mM citrate. In one embodiment of the invention, the pharmaceutical composition comprises 40 mM nicotinamide and 10 mM citrate. In one embodiment of the invention, the pharmaceutical composition comprises 60 mM nicotinamide and 10 mM citrate. In one embodiment of the invention, the pharmaceutical composition comprises 80 mM nicotinamide and 10 mM citrate. In one embodiment of the invention, the pharmaceutical composition comprises 100 mM nicotinamide and 10 mM citrate. In one embodiment of the invention, the pharmaceutical composition comprises 120 mM nicotinamide and 10 mM citrate. In one embodiment of the invention, the pharmaceutical composition comprises 140 mM nicotinamide and 10 mM citrate. In one embodiment of the invention, the pharmaceutical composition comprises 160 mM nicotinamide and 10 mM citrate. In one embodiment of the invention, the pharmaceutical composition comprises 170 mM nicotinamide and 10 mM citrate.

In one embodiment, a pharmaceutical composition comprises about 0.6 to about 3.6 mM insulin analogue A9E, B3E, B26E, desB30 or A9E, B3E, B27E, B28E, desB30 and further comprises of about 0.6 mg/ml to about 4 mg/ml of phenol, about 0.6 mg/ml to about 4 mg/ml of m-cresol, of about 0 to about 250 mM glycerol, of about 0.1 mM to about 20 mMTris or phosphate, of about 0 mM of nicotinamide and is having a pH value of about 7.0 to about 8.0.

In one embodiment, a pharmaceutical composition comprises about 0.6 to about 3.6 mM insulin analogue A9E, B3E, B26E, desB30 or A9E, B3E, B27E, B28E, desB30 and further comprises of about 0.6 mg/ml to about 4 mg/ml of phenol, about 0.6 mg/ml to about 4 mg/ml of m-cresol, of about 0 to about 250 mM glycerol, of about 0.1 mM to about 20 mMTris or phosphate, of about 40 mM of nicotinamide and is having a pH value of about 7.0 to about 8.0.

In one embodiment, a pharmaceutical composition comprises about 0.6 to about 3.6 mM insulin analogue A9E, B3E, B26E, desB30 or A9E, B3E, B27E, B28E, desB30 and further comprises of about 0.6 mg/ml to about 4 mg/ml of phenol, about 0.6 mg/ml to about 4 mg/ml of m-cresol, of about 0 to about 250 mM glycerol, of about 0.1 mM to about 20 mM.Tris or phosphate, of about 20 mM of nicotinamide, of about 10 mM of citrate and is having a pH value of about 7.0 to about 8.0.

The pharmaceutical composition of the invention may further comprise an amount of an amino acid base sufficient to decrease aggregate formation by the polypeptide or protein during storage of the composition. The term "amino acid base" refers to an amino acid or a combination of amino acids, where any given amino acid is present either in its free base form or in its salt form.

The invention further relates to a method for the preparation of such insulin preparations.

The insulin preparations of this invention can be prepared by using any of a number of recognized methods. For example, the preparations can be prepared by mixing an aqueous solution of excipients with an aqueous solution of the insulin analogue, after which the pH is adjusted to a desired level and the mixture is made up to the final volume with water followed by sterile filtration.

In one embodiment, the insulin analogue of the invention is monomeric in a pharmaceutical composition.

In one embodiment, the insulin analogue of the invention has reduced self-association properties in a pharmaceutical composition.

In one embodiment, the insulin analogue of the invention is chemically stable in a pharmaceutical composition.

In one embodiment, the insulin analogue of the invention is physically stable in a pharmaceutical composition.

In one embodiment, the insulin analogue of the invention is chemically and physically stable in a pharmaceutical composition.

In one embodiment, the insulin analogue of the invention is monomeric and physically stable in a pharmaceutical composition.

In one embodiment, the insulin analogue of the invention is monomeric and chemically stable in a pharmaceutical composition.

In one embodiment, the insulin analogue of the invention is monomeric and chemically and physically stable in a pharmaceutical composition.

In one embodiment, the insulin analogue of the invention is monomeric and chemically and physically stable in a pharmaceutical composition even at a high concentration.

In one embodiment, the absorption rates for the insulin analogues of invention are faster when compared to Fiasp®.

In one embodiment, of the invention this difference will allow to further improve the insulin dosing algorithm for the closed loop system to increase time in range (i.e. the time patient's blood glucose is in the healthy range).

Zinc-Free Pharmaceutical Compositions

Insulin preparations traditionally comprise zinc added as e.g. the chloride or acetate salt to obtain an acceptable stability of the pharmaceutical preparation. However, it has surprisingly been found that the insulin analogues of the invention, while maintaining a reduced self-association, sufficient chemical and physical stability, may be formulated into pharmaceutical compositions with high insulin concentration but without the addition of zinc, thereby giving a faster onset of action than comparable insulin analogues that need Zn2+ ions for maintaining sufficient chemical and physical stability. The zinc-free compositions are faster absorbed from the subcutaneous tissue, and thus allowing for prandial use.

However, provided zinc-free excipients can be provided, the insulin analogues of the present invention in fact allows for the preparation of zinc-free pharmaceutical compositions. Therefore, in one aspect, the invention provides "zinc-free pharmaceutical compositions" comprising an insulin analogue of the invention, and one or more pharmaceutically acceptable excipients, devoid of any zinc or with no added zinc ions.

The insulin analogue of the present invention adds to both the chemical and physical stability of a pharmaceutical compositions formulated without addition of zinc-ions and with no added surfactants.

In one embodiment, the pharmaceutical composition of the present invention is zinc free.

In one embodiment, the pharmaceutical composition comprising insulin analogue of the invention is zinc-free.

In one embodiment, the insulin analogue of the invention is monomeric in a zinc free pharmaceutical composition.

In one embodiment, the insulin analogue of the invention is chemically stable in a zinc free pharmaceutical composition.

In one embodiment, the insulin analogue of the invention is physically stable in a zinc free pharmaceutical composition.

In one embodiment, the insulin analogue of the invention is chemically and physically stable in a zinc free pharmaceutical composition.

In one embodiment, the insulin analogue of the invention is monomeric and chemically and physically stable in a zinc free pharmaceutical composition.

In one embodiment, the insulin analogue of the invention is monomeric and chemically and physically stable, even at high concentration, in a zinc free pharmaceutical composition.

Methods of Administration

The pharmaceutical composition of the invention may be administered by conventional methods.

Parenteral administration may be performed by subcutaneous, intramuscular, intraperitoneal or intravenous injection by means of a syringe, optionally a pen-like syringe. Alternatively, parenteral administration can be performed by means of an infusion pump. As a further option, the insulin preparations containing the insulin compound of the invention can also be adapted to transdermal administration, e.g. by needle-free injection or from a microneedle patch, optionally an iontophoretic patch, or transmucosal, e.g. buccal, administration.

The pharmaceutical composition of the invention may be administered to a patient in need of such treatment at several sites, for example, at topical sites, for example, skin and mucosal sites, at sites which bypass absorption, for example, administration in an artery, in a vein, in the heart, and at sites which involve absorption, for example, administration in the skin, under the skin, in a muscle or in the abdomen.

The pharmaceutical composition of the invention may be used in the treatment of diabetes by parenteral administration. The actual dosage depends on the nature and severity of the disease being treated, and is within the discretion of the physician, and may be varied by titration of the dosage to the particular circumstances of this invention to produce the desired therapeutic effect. The pharmaceutical compositions of the invention may also be prepared for use in various medical devices normally used for the administration of insulin, including pen-like devices used for insulin therapy by injection, continuous subcutaneous insulin infusion therapy by use of pumps.

In one embodiment the pharmaceutical composition of the invention is formulated into a pen-like device for use for insulin therapy by injection.

In one embodiment the pharmaceutical composition of the invention is formulated into an external pump for insulin administration.

In one embodiment the pharmaceutical composition of the invention is formulated into an insulin pump for insulin administration.

In one embodiment the pharmaceutical composition of the invention is suitable for insulin pump for insulin administration.

In one embodiment the pharmaceutical composition of the invention is suitable for insulin pump that can hold insulin analogues equivalent to 100-600 U of human insulin.

Methods of Therapy

The present invention relates to drugs for therapeutic use. More specifically the invention relates to the use of insulin analogues of the invention for the treatment or prevention of medical conditions relating to diabetes.

In one embodiment, the invention provides a method for the treatment or alleviation of a disease or disorder or condition of a living animal body, including a human, which disease, disorder or condition may be selected from a disease, disorder or condition relating to diabetes, Type 1 diabetes, Type 2 diabetes, impaired glucose tolerance, hyperglycemia, dyslipidemia, obesity, metabolic syndrome (metabolic syndrome X, insulin resistance syndrome), hypertension, cognitive disorders, which method comprises the step of administering to a subject in need thereof a therapeutically effective amount of the analogue of human insulin of the invention.

In one embodiment the invention provides a method for the treatment or alleviation of a disease or disorder or condition of a living animal body, including a human, which disease, disorder or condition may be selected from a disease, disorder or condition relating to diabetes, Type 1 diabetes, Type 2 diabetes, impaired glucose tolerance, hyperglycemia, dyslipidemia, obesity, or metabolic syndrome (metabolic syndrome X, insulin resistance syndrome).

In one embodiment the invention provides a method for the treatment or alleviation of a disease or disorder or condition of a living animal body, including a human, which disease, disorder or condition may be selected from a disease, disorder or condition relating to diabetes, in particular Type 1 diabetes, or Type 2 diabetes.

In one embodiment, the invention relates to the medical use of the insulin analogue of the invention, and in particular to the use of such insulin analogues for the treatment, prevention or alleviation of diseases, disorders or conditions relating to diabetes, Type 1 diabetes, Type 2 diabetes, impaired glucose tolerance, hyperglycemia, dyslipidemia, obesity, metabolic syndrome (metabolic syndrome X, insulin resistance syndrome), hypertension, cognitive disorders, which method comprises administration to a subject in need thereof a therapeutically effective amount of the insulin analogue of the invention.

In another embodiment, the invention relates to the use of such insulin analogues for the treatment, prevention or alleviation of diseases, disorders or conditions relating to diabetes, Type 1 diabetes, Type 2 diabetes, or impaired glucose tolerance, which method comprises administration to a subject in need thereof a therapeutically effective amount of the insulin analogues of the invention.

In another embodiment, the invention relates to the use of such insulin analogues for the treatment, prevention or alleviation of diseases, disorders or conditions relating to diabetes, and in particular Type 1 diabetes or Type 2 diabetes.

EMBODIMENTS

The invention is further described by the following non-limiting embodiments:

1. An insulin analogue, wherein the analogue comprises A9E or A9D and further comprises B3E and/or desB30 relative to human insulin.
2. The insulin analogue according to embodiment 1, wherein the analogue comprises A9E or A9D and further comprises B3E relative to human insulin.
3. The insulin analogue according to embodiment 1, wherein the analogue comprises A9E or A9D and further comprises desB30 relative to human insulin.
4. The insulin analogue according to embodiment 1, wherein the analogue comprises A9E or A9D and further comprises B3E and desB30 relative to human insulin.
5. The insulin analogue according to embodiment 2-4, wherein the analogue further comprises at least one of B26E, B27E and/or B28E.
6. The insulin analogue according to any one of embodiments 2-4, wherein the analogue further comprises B26E.
7. The insulin analogue according to any one of embodiments 2-4, wherein the analogue further comprises B27E.
8. The insulin analogue according to any one of embodiments 2-4, wherein the analogue further comprises B28E.
9. The insulin analogue according to any one of embodiments 2-4, wherein the analogue further comprises B26E and B27E.
10. The insulin analogue according to any one of embodiments 2-4, wherein the analogue further comprises B26E and B28E.
11. The insulin analogue according to any one of embodiments 2-4, wherein the analogue further comprises B27E and B28E.
12. The insulin analogue according to any one of embodiments 2-4, wherein the analogue further comprises B26E, B27E and B28E.
13. The insulin analogue according to any one of the embodiments 5-12, wherein the analogue additionally comprises the A21A substitution.
14. The insulin analogue according to any of the preceding embodiments, wherein the analogue is
A9D, B3E;
A9E, B3E;
A9D, desB30;
A9E, desB30;
A9D, B3E, desB30;
A9E, B3E, desB30;
A9D, B3E, B26E;
A9E, B3E, B26E;
A9D, B26E, desB30;
A9E, B26E, desB30;
A9D, B3E, B26E, desB30;
A9E, B3E, B26E, desB30;
A9D, A21A, B3E, B26E;
A9E, A21A, B3E, B26E;
A9D, A21A, B26E, desB30;
A9E, A21A, B26E, desB30;
A9D, A21A, B3E, B26E, desB30;
A9E, A21A, B3E, B26E, desB30;
A9D, B3E, B27E;
A9E, B3E, B27E;
A9D, B27E, desB30;
A9E, B27E, desB30;
A9D, B3E, B27E, desB30;
A9E, B3E, B27E, desB30;
A9D, A21A, B3E, B27E;
A9E, A21A, B3E, B27E;
A9D, A21A, B27E, desB30;
A9E, A21A, B27E, desB30;
A9D, A21A, B3E, B27E, desB30;
A9E, A21A, B3E, B27E, desB30;
A9D, B3E, B28E;
A9E, B3E, B28E;
A9D, B28E, desB30;
A9E, B28E, desB30;
A9D, B3E, B28E, desB30;
A9E, B3E, B28E, desB30;
A9D, A21A, B3E, B28E;
A9E, A21A, B3E, B28E;
A9D, A21A, B28E, desB30;
A9E, A21A, B28E, desB30;
A9D, A21A, B3E, B28E, desB30;
A9E, A21A, B3E, B28E, desB30;
A9D, B3E, B26E, B27E;
A9E, B3E, B26E, B27E;
A9D, B26E, B27E, desB30;
A9E, B26E, B27E, desB30;
A9D, B3E, B26E, B27E, desB30;
A9E, B3E, B26E, B27E, desB30;
A9D, A21A, B3E, B26E, B27E;
A9E, A21A, B3E, B26E, B27E;
A9D, A21A, B26E, B27E, desB30;
A9E, A21A, B26E, B27E, desB30;
A9D, A21A, B3E, B26E, B27E, desB30;
A9E, A21A, B3E, B26E, B27E, desB30;
A9D, B3E, B27E, B28E;
A9E, B3E, B27E, B28E;
A9D, B27E, B28E, desB30;
A9E, B27E, B28E, desB30;
A9D, B3E, B27E, B28E, desB30;
A9E, B3E, B27E, B28E, desB30;
A9D, A21A, B3E, B27E, B28E;
A9E, A21A, B3E, B27E, B28E;
A9D, A21A, B27E, B28E, desB30;
A9E, A21A, B27E, B28E, desB30;
A9D, A21A, B3E, B27E, B28E, desB30;
A9E, A21A, B3E, B27E, B28E, desB30;
A9D, B3E, B26E, B28E;
A9E, B3E, B26E, B28E;
A9D, B26E, B28E, desB30;
A9E, B26E, B28E, desB30;
A9D, B3E, B26E, B28E, desB30;
A9E, B3E, B26E, B28E, desB30;
A9D, A21A, B3E, B26E, B28E;

A9E, A21A, B3E, B26E, B28E;
A9D, A21A, B26E, B28E, desB30;
A9E, A21A, B26E, B28E, desB30;
A9D, A21A, B3E, B26E, B28E, desB30;
A9E, A21A, B3E, B26E, B28E, desB30;
A9D, B3E, B26E, B27E, B28E;
A9E, B3E, B26E, B27E, B28E;
A9D, B26E, B27E, B28E, desB30;
A9E, B26E, B27E, B28E, desB30;
A9D, B3E, B26E, B27E, B28E, desB30;
A9E, B3E, B26E, B27E, B28E, desB30;
A9D, A21A, B3E, B26E, B27E, B28E;
A9E, A21A, B3E, B26E, B27E, B28E;
A9D, A21A, B26E, B27E, B28E, desB30;
A9E, A21A, B26E, B27E, B28E, desB30;
A9D, A21A, B3E, B26E, B27E, B28E, desB30; or
A9E, A21A, B3E, B26E, B27E, B28E, desB30.

15. The insulin analogue according to embodiment 14, wherein the analogue is
A9D, B3E, B26E;
A9E, B3E, B26E;
A9D, B26E, desB30;
A9E, B26E, desB30;
A9D, B3E, B26E, desB30;
A9E, B3E, B26E, desB30;
A9D, A21A, B3E, B26E;
A9E, A21A, B3E, B26E;
A9D, A21A, B26E, desB30;
A9E, A21A, B26E, desB30;
A9D, A21A, B3E, B26E, desB30;
A9E, A21A, B3E, B26E, desB30;
A9D, B3E, B27E;
A9E, B3E, B27E;
A9D, B27E, desB30;
A9E, B27E, desB30;
A9D, B3E, B27E, desB30;
A9E, B3E, B27E, desB30;
A9D, A21A, B3E, B27E;
A9E, A21A, B3E, B27E;
A9D, A21A, B27E, desB30;
A9E, A21A, B27E, desB30;
A9D, A21A, B3E, B27E, desB30;
A9E, A21A, B3E, B27E, desB30;
A9D, B3E, B28E;
A9E, B3E, B28E;
A9D, B28E, desB30;
A9E, B28E, desB30;
A9D, B3E, B28E, desB30;
A9E, B3E, B28E, desB30;
A9D, A21A, B3E, B28E;
A9E, A21A, B3E, B28E;
A9D, A21A, B28E, desB30;
A9E, A21A, B28E, desB30;
A9D, A21A, B3E, B28E, desB30;
A9E, A21A, B3E, B28E, desB30;
A9D, B3E, B26E, B27E;
A9E, B3E, B26E, B27E;
A9D, B26E, B27E, desB30;
A9E, B26E, B27E, desB30;
A9D, B3E, B26E, B27E, desB30;
A9E, B3E, B26E, B27E, desB30;
A9D, A21A, B3E, B26E, B27E;
A9E, A21A, B3E, B26E, B27E;
A9D, A21A, B26E, B27E, desB30;
A9E, A21A, B26E, B27E, desB30;
A9D, A21A, B3E, B26E, B27E, desB30;
A9E, A21A, B3E, B26E, B27E, desB30;
A9D, B3E, B27E, B28E;
A9E, B3E, B27E, B28E;
A9D, B27E, B28E, desB30;
A9E, B27E, B28E, desB30;
A9D, B3E, B27E, B28E, desB30;
A9E, B3E, B27E, B28E, desB30;
A9D, A21A, B3E, B27E, B28E;
A9E, A21A, B3E, B27E, B28E;
A9D, A21A, B27E, B28E, desB30;
A9E, A21A, B27E, B28E, desB30;
A9D, A21A, B3E, B27E, B28E, desB30;
A9E, A21A, B3E, B27E, B28E, desB30;
A9D, B3E, B26E, B28E;
A9E, B3E, B26E, B28E;
A9D, B26E, B28E, desB30;
A9E, B26E, B28E, desB30;
A9D, B3E, B26E, B28E, desB30;
A9E, B3E, B26E, B28E, desB30;
A9D, A21A, B3E, B26E, B28E;
A9E, A21A, B3E, B26E, B28E;
A9D, A21A, B26E, B28E, desB30;
A9E, A21A, B26E, B28E, desB30;
A9D, A21A, B3E, B26E, B28E, desB30;
A9E, A21A, B3E, B26E, B28E, desB30;
A9D, B3E, B26E, B27E, B28E;
A9E, B3E, B26E, B27E, B28E;
A9D, B26E, B27E, B28E, desB30;
A9E, B26E, B27E, B28E, desB30;
A9D, B3E, B26E, B27E, B28E, desB30;
A9E, B3E, B26E, B27E, B28E, desB30;
A9D, A21A, B3E, B26E, B27E, B28E;
A9E, A21A, B3E, B26E, B27E, B28E;
A9D, A21A, B26E, B27E, B28E, desB30;
A9E, A21A, B26E, B27E, B28E, desB30;
A9D, A21A, B3E, B26E, B27E, B28E, desB30; or
A9E, A21A, B3E, B26E, B27E, B28E, desB30.

16. The insulin analogue according to embodiment 15, wherein the analogue is
A9D, B3E, B26E;
A9E, B3E, B26E;
A9D, B26E, desB30;
A9E, B26E, desB30;
A9D, B3E, B26E, desB30;
A9E, B3E, B26E, desB30;
A9D, A21A, B3E, B26E;
A9E, A21A, B3E, B26E;
A9D, A21A, B26E, desB30;
A9E, A21A, B26E, desB30;
A9D, A21A, B3E, B26E, desB30;
A9E, A21A, B3E, B26E, desB30;
A9D, A21A, B3E, B28E, desB30;
A9E, A21A, B3E, B28E, desB30;
A9D, B3E, B26E, B27E;
A9E, B3E, B26E, B27E;
A9D, B26E, B27E, desB30;
A9E, B26E, B27E, desB30;
A9D, B3E, B26E, B27E, desB30;
A9E, B3E, B26E, B27E, desB30;
A9D, A21A, B3E, B26E, B27E;
A9E, A21A, B3E, B26E, B27E;
A9D, A21A, B26E, B27E, desB30;
A9E, A21A, B26E, B27E, desB30;
A9D, A21A, B3E, B26E, B27E, desB30;
A9E, A21A, B3E, B26E, B27E, desB30;
A9D, B3E, B27E, B28E;
A9E, B3E, B27E, B28E;
A9D, B27E, B28E, desB30;

A9E, B27E, B28E, desB30;
A9D, B3E, B27E, B28E, desB30;
A9E, B3E, B27E, B28E, desB30;
A9D, A21A, B3E, B27E, B28E;
A9E, A21A, B3E, B27E, B28E;
A9D, A21A, B27E, B28E, desB30;
A9E, A21A, B27E, B28E, desB30;
A9D, A21A, B3E, B27E, B28E, desB30;
A9E, A21A, B3E, B27E, B28E, desB30;
A9D, B3E, B26E, B28E;
A9E, B3E, B26E, B28E;
A9D, B26E, B28E, desB30;
A9E, B26E, B28E, desB30;
A9D, B3E, B26E, B28E, desB30;
A9E, B3E, B26E, B28E, desB30;
A9D, A21A, B3E, B26E, B28E;
A9E, A21A, B3E, B26E, B28E;
A9D, A21A, B26E, B28E, desB30;
A9E, A21A, B26E, B28E, desB30;
A9D, A21A, B3E, B26E, B28E, desB30;
A9E, A21A, B3E, B26E, B28E, desB30;
A9D, B3E, B26E, B27E, B28E;
A9E, B3E, B26E, B27E, B28E;
A9D, B26E, B27E, B28E, desB30;
A9E, B26E, B27E, B28E, desB30;
A9D, B3E, B26E, B27E, B28E, desB30;
A9E, B3E, B26E, B27E, B28E, desB30;
A9D, A21A, B3E, B26E, B27E, B28E;
A9E, A21A, B3E, B26E, B27E, B28E;
A9D, A21A, B26E, B27E, B28E, desB30;
A9E, A21A, B26E, B27E, B28E, desB30;
A9D, A21A, B3E, B26E, B27E, B28E, desB30; or
A9E, A21A, B3E, B26E, B27E, B28E, desB30.

17. The insulin analogue according to embodiment 16, wherein the analogue is
A9D, B3E, B26E;
A9E, B3E, B26E;
A9D, B3E, B26E, desB30;
A9E, B3E, B26E, desB30;
A9D, A21A, B3E, B26E;
A9E, A21A, B3E, B26E;
A9D, A21A, B3E, B26E, desB30;
A9E, A21A, B3E, B26E, desB30;
A9D, A21A, B3E, B28E, desB30;
A9E, A21A, B3E, B28E, desB30;
A9D, B3E, B26E, B27E;
A9E, B3E, B26E, B27E;
A9D, B3E, B26E, B27E, desB30;
A9E, B3E, B26E, B27E, desB30;
A9D, A21A, B3E, B26E, B27E;
A9E, A21A, B3E, B26E, B27E;
A9D, A21A, B3E, B26E, B27E, desB30;
A9E, A21A, B3E, B26E, B27E, desB30;
A9D, B3E, B27E, B28E;
A9E, B3E, B27E, B28E;
A9D, B3E, B27E, B28E, desB30;
A9E, B3E, B27E, B28E, desB30;
A9D, A21A, B3E, B27E, B28E;
A9E, A21A, B3E, B27E, B28E;
A9D, A21A, B3E, B27E, B28E, desB30;
A9E, A21A, B3E, B27E, B28E, desB30;
A9D, B3E, B26E, B28E;
A9E, B3E, B26E, B28E;
A9D, B3E, B26E, B28E, desB30;
A9E, B3E, B26E, B28E, desB30;
A9D, A21A, B3E, B26E, B28E;
A9E, A21A, B3E, B26E, B28E;
A9D, A21A, B3E, B26E, B28E, desB30;
A9E, A21A, B3E, B26E, B28E, desB30;
A9D, B3E, B26E, B27E, B28E;
A9E, B3E, B26E, B27E, B28E;
A9D, B3E, B26E, B27E, B28E, desB30;
A9E, B3E, B26E, B27E, B28E, desB30;
A9D, A21A, B3E, B26E, B27E, B28E;
A9E, A21A, B3E, B26E, B27E, B28E;
A9D, A21A, B3E, B26E, B27E, B28E, desB30; or
A9E, A21A, B3E, B26E, B27E, B28E, desB30.

18. The insulin analogue according to embodiment 17, wherein the analogue is
A9E, B3E, B26E;
A9E, B3E, B27E, B28E;
A9E, B3E, B26E, desB30;
A9E, B3E, B27E, B28E, desB30;
A9D, B3E, B26E, desB30; or
A9E, A21A, B3E, B26E, desB30.

19. The insulin analogue according to embodiment 18, wherein the analogue is A9E, B3E, B26E.

20. The insulin analogue according to embodiment 18, wherein the analogue is A9E, B3E, B27E, B28E.

21. The insulin analogue according to embodiment 18, wherein the analogue is A9E, B3E, B26E, desB30.

22. The insulin analogue according to embodiment 18, wherein the analogue is A9E, B3E, B27E, B28E, desB30.

23. The insulin analogue according to embodiment 18, wherein the analogue is A9D, B3E, B26E, desB30.

24. The insulin analogue according to embodiment 18, wherein the analogue is A9E, A21A, B3E, B26E, desB30.

25. A pharmaceutical composition comprising an insulin analogue according to any one of embodiments 1-24, and one or more pharmaceutically acceptable excipients.

26. The pharmaceutical composition according to embodiment 25, comprising an insulin analogue, which is A9E, B3E, B26E, desB30.

27. The pharmaceutical composition according to embodiment 25, comprising an insulin analogue, which is A9E, B3E, B27E, B28E, desB30.

28. The pharmaceutical composition according to embodiment 25, comprising an insulin analogue, which is A9D, B3E, B26E, desB30.

29. The pharmaceutical composition according to embodiment 25, comprising an insulin analogue, which is A9E, A21A, B3E, B26E, desB30.

30. The pharmaceutical composition according to embodiments 25-29, wherein the insulin analogue is in a concentration of from about 0.1 mM to about 20.0 mM.

31. The pharmaceutical composition according to embodiments 25-30, wherein the insulin analogue is in a concentration of from about 0.6 to about 3.6 mM.

32. The pharmaceutical composition according to embodiment 31, wherein the insulin analogue is in a concentration of about 0.6 mM.

33. The pharmaceutical composition according to embodiment 31, wherein the insulin analogue is in a concentration of about 1.2 mM.

34. The pharmaceutical composition according to embodiment 31, wherein the insulin analogue is in a concentration of about 1.8 mM.

35. The pharmaceutical composition according to embodiment 31, wherein the insulin analogue is in a concentration of about 2.4 mM.

36. The pharmaceutical composition according to embodiment 31, wherein the insulin analogue is in a concentration of about 3.0 mM.

37. The pharmaceutical composition according to embodiment 25-29, wherein the insulin analogue is in a concentration of about 100-600U.

38. The pharmaceutical composition according to embodiments 37, wherein the insulin analogue is in a concentration of about 100U.

39. The pharmaceutical composition according to embodiments 37, wherein the insulin analogue is in a concentration of about 200U.

40. The pharmaceutical composition according to embodiments 37, wherein the insulin analogue is in a concentration of about 300U.

41. The pharmaceutical composition according to embodiments 37, wherein the insulin analogue is in a concentration of about 400U.

42. The pharmaceutical composition according to embodiments 37, wherein the insulin analogue is in a concentration of about 500U.

43. The pharmaceutical composition according to embodiments 37, wherein the insulin analogue is in a concentration of about 600U.

44. The pharmaceutical composition according to embodiments 25-43, wherein the composition is free of zinc.

45. The pharmaceutical composition according to embodiments 25-44 comprising a nicotinic compound, and in particular nicotinamide.

46. The pharmaceutical composition according to embodiments 25-45, comprising nicotinamide in a concentration from about 0 mM to about 200 mM.

47. The pharmaceutical composition according to embodiment 46, comprising 10 mM nicotinamide.

48. The pharmaceutical composition according to embodiments 46, comprising 20 mM nicotinamide.

49. The pharmaceutical composition according to embodiment 46, comprising 40 mM nicotinamide.

50. The pharmaceutical composition according to embodiments 46, comprising 170 mM nicotinamide.

51. The pharmaceutical composition according to embodiments 25-50 embodiments, comprising of from about 0.6 mg/ml to about 4 mg/ml of phenol and/or m-cresol.

52. The pharmaceutical composition according to embodiment 51, comprising about 1.5 mg/ml phenol and about 1.72 mg/ml m-cresol.

53. The pharmaceutical composition according to embodiment 51, comprising about 1.79 mg/ml phenol and about 2.05 mg/ml m-cresol.

54. The pharmaceutical composition according to embodiments 25-53, comprising glycerol in a concentration of from 0 to about 250 mM.

55. The pharmaceutical composition according to embodiment 54, comprising about 103 mM, 130 mM, 163 mM, 185 mM, 195 mM, 200 mM, 230 mM or 233 mM glycerol.

56. The pharmaceutical composition according to embodiments 25-55, comprising propylene glycol in a concentration of about 0-2%.

57. The pharmaceutical composition according to embodiment 56 comprising propylene glycol in a concentration of about 1.5%.

58. The pharmaceutical composition according to embodiments 25-57, comprising buffer in a concentration of about 0.1 mM to 20 mM.

59. The pharmaceutical composition according to embodiment 58, comprising phosphate buffer in a concentration of about 3 mM.

60. The pharmaceutical composition according to embodiment 58, comprising Tris buffer in a concentration of about 7 mM.

61. The pharmaceutical composition according to embodiments 25-60, which has a pH value in the range of from about 7.0 to about 8.0.

62. The pharmaceutical composition according to embodiment 61, which has a pH value in the range of from about 7.2 to about 7.8.

63. The pharmaceutical composition according to the embodiment 62, which has a pH value in the range of from about 7.4 to about 7.6.

64. The pharmaceutical composition according to embodiments 25-63, comprising citrate.

65. The pharmaceutical composition according to embodiment 64, comprising citrate in a concentration from 1 mM to 50 mM.

66. The pharmaceutical composition according to embodiment 65, comprising citrate in a concentration of 5 mM.

67. The pharmaceutical composition according to embodiments 65, comprising citrate in a concentration of 10 mM.

68. The pharmaceutical composition according to embodiment 65, comprising citrate in a concentration of 15 mM.

69. The pharmaceutical composition according to embodiment 65, comprising citrate in a concentration of 20 mM.

70. The pharmaceutical composition according to preceding embodiments, comprising 10 mM nicotinamide and 10 mM citrate.

71. The pharmaceutical composition according to preceding embodiments, comprising 20 mM nicotinamide and 10 mM citrate.

72. The pharmaceutical composition according to preceding embodiments, comprising 40 mM nicotinamide and 10 mM citrate.

73. The pharmaceutical composition according to preceding embodiments, comprising 0.6 mM of insulin analogue A9E, B3E, B26E, desB30;
   1.5 mg/ml phenol;
   1.72 mg/ml m-cresol;
   233 mM glycerol;
   3 mM phosphate;
   0 mM of nicotinamide; and
   pH of 7.4.

74. The pharmaceutical composition according to preceding embodiments, comprising 1.2 mM of insulin analogue A9E, B3E, B26E, desB30;
   1.5 mg/ml phenol;
   1.72 mg/ml m-cresol;
   233 mM glycerol;
   3 mM phosphate;
   0 mM of nicotinamide; and
   pH of 7.4.

75. The pharmaceutical composition according to preceding embodiments, comprising 1.8 mM of insulin analogue A9E, B3E, B26E, desB30;
   1.5 mg/ml phenol;
   1.72 mg/ml m-cresol;
   233 mM glycerol;
   3 mM phosphate;
   0 mM of nicotinamide; and
   pH of 7.4.

76. The pharmaceutical composition according to preceding embodiments, comprising 2.4 mM of insulin analogue A9E, B3E, B26E, desB30;
  1.5 mg/ml phenol;
  1.72 mg/ml m-cresol;
  233 mM glycerol;
  3 mM phosphate;
  0 mM of nicotinamide; and
  pH of 7.4.

77. The pharmaceutical composition according to preceding embodiments, comprising 3.0 mM of insulin analogue A9E, B3E, B26E, desB30;
  1.5 mg/ml phenol;
  1.72 mg/ml m-cresol;
  233 mM glycerol;
  3 mM phosphate;
  0 mM of nicotinamide; and
  pH of 7.4.

78. The pharmaceutical composition according to preceding embodiments, comprising 0.6 mM of insulin analogue A9E, B3E, B26E, desB30;
  1.5 mg/ml phenol;
  1.72 mg/ml m-cresol;
  200 mM glycerol;
  3 mM phosphate;
  40 mM of nicotinamide; and
  pH of 7.4.

79. The pharmaceutical composition according to preceding embodiments, comprising 1.2 mM of insulin analogue A9E, B3E, B26E, desB30;
  1.5 mg/ml phenol;
  1.72 mg/ml m-cresol;
  200 mM glycerol;
  3 mM phosphate;
  40 mM of nicotinamide; and
  pH of 7.4.

80. The pharmaceutical composition according to preceding embodiments, comprising 1.8 mM of insulin analogue A9E, B3E, B26E, desB30;
  1.5 mg/ml phenol;
  1.72 mg/ml m-cresol;
  200 mM glycerol;
  3 mM phosphate;
  40 mM of nicotinamide; and
  pH of 7.4.

81. The pharmaceutical composition according to preceding embodiments, comprising 2.4 mM of insulin analogue A9E, B3E, B26E, desB30;
  1.5 mg/ml phenol;
  1.72 mg/ml m-cresol;
  200 mM glycerol;
  3 mM phosphate;
  40 mM of nicotinamide; and
  pH of 7.4.

82. The pharmaceutical composition according to preceding embodiments, comprising 3.0 mM of insulin analogue A9E, B3E, B26E, desB30;
  1.5 mg/ml phenol;
  1.72 mg/ml m-cresol;
  200 mM glycerol;
  3 mM phosphate;
  40 mM of nicotinamide; and
  pH of 7.4.

83. The pharmaceutical composition according to preceding embodiments, comprising 0.6 mM of insulin analogue A9E, B3E, B26E, desB30;
  1.5 mg/ml phenol;
  1.72 mg/ml m-cresol;
  185 mM glycerol;
  3 mM phosphate;
  20 mM of nicotinamide;
  10 mM of citrate; and
  pH of 7.4.

84. The pharmaceutical composition according to preceding embodiments, comprising 1.2 mM of insulin analogue A9E, B3E, B26E, desB30;
  1.5 mg/ml phenol;
  1.72 mg/ml m-cresol;
  185 mM glycerol;
  3 mM phosphate;
  20 mM of nicotinamide;
  10 mM of citrate; and
  pH of 7.4.

85. The pharmaceutical composition according to preceding embodiments, comprising 1.8 mM of insulin analogue A9E, B3E, B26E, desB30;
  1.5 mg/ml phenol;
  1.72 mg/ml m-cresol;
  185 mM glycerol;
  3 mM phosphate;
  20 mM of nicotinamide;
  10 mM of citrate; and
  pH of 7.4.

86. The pharmaceutical composition according to preceding embodiments, comprising 2.4 mM of insulin analogue A9E, B3E, B26E, desB30;
  1.5 mg/ml phenol;
  1.72 mg/ml m-cresol;
  185 mM glycerol;
  3 Mm phosphate;
  20 mM of nicotinamide;
  10 mM of citrate; and
  pH of 7.4.

87. The pharmaceutical composition according to preceding embodiments, comprising 3.0 mM of insulin analogue A9E, B3E, B26E, desB30;
  1.5 mg/ml phenol;
  1.72 mg/ml m-cresol;
  185 mM glycerol;
  3 mM phosphate;
  20 mM of nicotinamide;
  10 mM of citrate; and
  pH of 7.4.

88. The pharmaceutical composition according to preceding embodiments, comprising 0.6 mM, 1.2 mM, 1.8 mM, 2.4 mM or 3.0 mM of insulin analogue A9E, B3E, B27E, B28E, desB30;
  1.5 mg/ml phenol;
  1.72 mg/ml m-cresol;
  233 mM glycerol;
  3 mM phosphate;
  0 mM of nicotinamide; and
  pH of 7.4.

89. The pharmaceutical composition according to preceding embodiments, comprising 0.6 mM, 1.2 mM, 1.8 mM, 2.4 mM or 3.0 mM of insulin analogue A9E, B3E, B27E, B28E, desB30;
  1.5 mg/ml phenol;
  1.72 mg/ml m-cresol;
  200 mM glycerol;
  3 mM phosphate;
  40 mM of nicotinamide; and
  pH of 7.4.

90. The pharmaceutical composition according to preceding embodiments, comprising 0.6 mM, 1.2 mM, 1.8 mM, 2.4 mM or 3.0 mM of insulin analogue A9E, B3E, B27E, B28E, desB30;
- 1.5 mg/ml phenol;
- 1.72 mg/ml m-cresol;
- 185 mM glycerol;
- 3 mM phosphate;
- 20 mM of nicotinamide;
- 10 mM of citrate; and
- pH of 7.4.

91. The insulin analogue according to any one of embodiments 1-24 or a pharmaceutically acceptable salt thereof or the pharmaceutical composition according to any one of embodiments 25-90, for use as a medicament.

92. The insulin analogue according to any one of embodiments 1-24 or a pharmaceutically acceptable salt thereof or the pharmaceutical composition according to any one of embodiments 25-90, for use in the prevention or alleviation or treatment of a disease or disorder or condition of a human body, wherein the disease, disorder or condition relates to diabetes, in particular Type 1 diabetes, or Type 2 diabetes.

93. A method of treatment, prevention or alleviation of a disease or disorder or condition of a human body, wherein the disease, disorder or condition relates to diabetes, in particular Type 1 diabetes, or Type 2 diabetes, wherein the method comprises the step of administering to such a living animal body in need thereof, a therapeutically effective amount of the insulin analogue according to any one of embodiments 1-24 or pharmaceutical composition according to any one embodiments 25-90.

EXAMPLES

Materials and Methods

LIST OF ABBREVIATIONS

ACN—Acetonitrile
ALP—Achromobacter lyticus protease
AUC—Area under the curve
C-peptide—connecting peptide
DCM—dichloromethane
DIC—diisopropylcarbodiimide;
DIPEA=DIEA—N, N-disopropylethylamine
DMF—N, N-dimethylformamide
DMSO—dimethyl sulphoxide
Fmoc—fluorenylmethoxycarbonyl
Glu (gGlu)—gamma L-glutamyl
HFIP—Hexafluoro-2-propanol
HPLC—high-performance liquid chromatography
IR—insulin receptor
IGF-1R insulin-like growth factor 1 receptor
LC—liquid chromatography
MALDI-TOF—matrix-assisted laser desorption ionisation time-of-flight
MS—mass spectrometry
NMP—N-methylpyrrolidone
PAL—Peptide Amide Linker
PCR—polymerase chain reaction
PD—pharmacodynamics (blood/plasma glucose lowering effect)
PK—pharmacodynamics (blood/plasma insulin concentrations versus time profiles)
RT—room temperature
tBu—tert-butyl
TFA—trifluoroacetic acid; and
TRIS—tris (hydroxy methyl) aminomethane.

General Methods of Preparation
General Procedure (A)
Solid Phase Synthesis and Purification of Analogues of the Invention A general procedure for the solid phase synthesis and purification of the insulin analogues of the invention is described in detail below and has been applied to the synthesis of additional compounds as indicated below.

Insulin A and B chains were prepared on a Prelude peptide synthesiser using a general Fmoc based solid phase peptide coupling method.

Resins Used:
Fmoc-Thr(OtBu)-Wang; and Fmoc-Asp-OtBu coupled to PAL resin.

Amino acids (listed below) and oxyma were dissolved in DMF to a concentration of 0.3 M:
Fmoc-Ala-OH; Fmoc-Arg(Pbf)-OH; Fmoc-Asn(Trt)-OH; Fmoc-Asp(OtBu)-OH; Fmoc-Cys(Trt)-OH; Fmoc-Gln(Trt)-OH; Fmoc-Glu(OtBu)-OH; Fmoc-Gly-OH; Fmoc-His(Trt)-OH; Fmoc-Ile-OH; Fmoc-Leu-OH; Fmoc-Lys(Boc)-OH; Fmoc-Met-OH; Fmoc-Phe-OH; Fmoc-Pro-OH; Fmoc-Ser(tBu)-OH; Fmoc-Thr(tBu)-OH; Fmoc-Trp(Boc)-OH; Fmoc-Tyr(tBu)-OH; and Fmoc-Val-OH.

Special/unnatural amino acids: Boc-Phe-OH; Boc-Gly-OH; and Fmoc-Cys(Acm)-OH.

Procedure
Scale: 0.25 mmol.
Standard coupling conditions used on resins were: 8 eq amino acid, DIC, collidine and oxyma (ethyl (hydroxyimino)cyanoacetate) in NMP for 1 hour, in the case of Fmoc-Arg(Pbf)-OH, a double coupling protocol (2×1h) was used.

Standard deprotection conditions used were: 20% piperdine in NMP (2×5.5 ml for 2×7.5 min or 2×10 min), followed by washing with NMP and DCM.

A6C-A11C Disulfide Formation
The resin was treated for 15 min with a 0.5% solution of iodine in DCM/HFIP (30 mL of 1:1 mixture). After removal of solvent by filtration the resin was washed with DCM (3×20 ml) and dried over a nitrogen stream.

A-Chain Cleavage from the Resin and Activation of A20-Cys as S—S-Pyridyl
The resin was treated with a solution of TFA (30 mL), triisopropylsilane (1 ml), water (0.75 ml) and dithiodipyridine (0.75 g) for 3 h, and then the filtrate was collected and added to 150 ml ether (split into 6 plastic NUNC tubes) to precipitate the peptide. The tubes were centrifuged at 3500 rpm for 3 min, the ether layer was decanted, and this ether step was repeated a further 3 times. The crude material was combined and allowed to dry overnight at RT to give the desired peptide A-chain.

B-Chain Cleavage from the Resin
The resin was treated with a solution of TFA (30 mL), triisopropylsilane (1 ml), water (0.75 ml) and dithiothreitol (0.5 g) for 3 h, and then the filtrate was collected and added to ether (150 ml, split into 6 plastic NUNC tubes) to precipitate the peptide. The tubes were centrifuged at 3500 rpm for 3 min, the ether layer was decanted, and this ether step was repeated a further 3 times. The crude material was allowed to dry overnight at RT to give the desired peptide B-chain.

A20C-B19C Disulfide Formation
To a mixture of A-chain (0.33 g) and B-chain (0.33 g) was added DMSO (8 mL) and DIPEA (1 mL) and the mixture stirred for 20 min, then added drop-wise with stirring to 140 ml of neutral buffer solution (water, TRIS (10 mM), ammonium sulphate (15 mM), 20% acetonitrile) to a total volume of approx. 150 ml.

The mixture was then purified by reverse phase chromatography using following set up Phenomenex Gemini 5 µM 5u C18 110 Å 30×250 mm column, running at 20 mL/min 10% B to 60% B over 40 min Eluant A-10 mM TRIS, 15 mM ammonium sulfate, pH=7.3, 20% ACN in milliQ water Eluant B-20% miliQ water in acetonitrile Pure fractions were pooled, flash frozen and freeze dried.

A7C-B7C Disulfide Formation

Freeze dried intermediate from the previous step was re-dissolved in 5 mL DMSO. Acetic acid (20 mL) and water (4 mL) was added, followed by iodine in AcOH (3 mL of 40 mM)

After total reaction time of 20 min, the reaction quenched with 1M sodium ascorbate, and then added to a stirred solution of water (90 mL).

The mixture was then purified by reverse phase chromatography using following set up Phenomenex Gemini 5 µM 5u C18 110 Å 30×250 mm column, running at 20 mL/min 10% B to 45% B over 40 min Eluant A-0.1% TFA in milliQ water Eluant B-0.1% TFA in acetonitrile Pure fractions were pooled, flash frozen and freeze dried to give the desired product.

General Procedure (B)

Insulin Analogue Expression and Purification

Insulin Analogue Expression in *S. cerevisiae*

The insulin analogue, i.e. the two-chain non-acylated insulin analogues, for use according to the invention are produced recombinantly by expressing a DNA sequence encoding the insulin analogue in question in a suitable host cel by well-known techniques, e.g. as disclosed in U.S. Pat. No. 6,500,645. The insulin analogue is either expressed directly or as a precursor molecule which may have an N-terminal extension on the B-chain and/or a connecting peptide (C-peptide) between the B-chain and the A-chain. This N-terminal extension and C-peptide are cleaved off in vitro by a suitable protease, e.g. Achromobactor lyticus protease (ALP) or trypsin, and will therefore have a cleavage site next to position B1 and A1, respectively. N-terminal extensions and C-peptides of the type suitable for use according to this invention are disclosed in e.g. U.S. Pat. No. 5,395,922, EP 765395 and WO 9828429.

The polynucleotide sequence encoding the insulin analogue precursor for use according to the invention may be prepared synthetically by established methods, e.g. the phosphoamidite method described by Beaucage et al. (1981) Tetrahedron Letters 22 1859-1869, or the method described by Matthes et al. (1984) EMBO Journal 3 801-805. According to the phosphoamidite method, oligonucleotides are synthesised in e.g. an automatic DNA synthesiser, purified, duplexed, and ligated to form the synthetic DNA construct. A currently preferred way of preparing the DNA construct is by polymerase chain reaction (PCR).

The recombinant method will typically make use of a vector which is capable of replicating in the selected microorganism or host cell and which carries a polynucleotide sequence encoding the insulin analogue precursor for use according to the present invention. The recombinant vector may be an autonomously replicating vector, i.e., a vector which exists as an extra-chromosomal entity, the replication of which is independent of chromosomal replication, e.g. a plasmid, an extra-chromosomal element, a mini-chromosome, or an artificial chromosome. The vector may contain any means for assuring self-replication. Alternatively, the vector may be one which, when introduced into the host cell, is integrated into the genome and replicated together with the chromosome(s) into which it has been integrated. Furthermore, a single vector or plasmid or two or more vectors or plasmids which together contain the total DNA to be introduced into the genome of the host cell, or a transposon may be used. The vector may be linear or closed circular plasmids and will preferably contain an element(s) that permits stable integration of the vector into the host cell's genome or autonomous replication of the vector in the cel independent of the genome.

The recombinant expression vector may be one capable of replicating in yeast. Examples of sequences which enable the vector to replicate in yeast are the yeast plasmid 2 µm replication genes REP 1-3 and origin of replication.

The vector may contain one or more selectable markers, which permit easy selection of trans-formed cells. A selectable marker is a gene product, which provides for biocide or viral resistance, resistance to heavy metals, prototrophy to auxotrophs, and the like. Examples of bacterial selectable markers are the dal genes from *Bacillus subtilis* or *Bacillus licheniformis*, or markers which confer antibiotic resistance such as ampicillin, kanamycin, chloramphenicol or tetracycline resistance. Selectable markers for use in a filamentous fungal host cel include amdS (acetamidase), argB (ornithine carbamoyltransferase), pyrG (orotidine-5'-phosphate decarboxylase) and trpC (anthranilate synthase). Suitable markers for yeast host cells are ADE2, HIS3, LEU2, LYS2, MET3, TRP1, and URA3. A well suited selectable marker for yeast is the *Schizosaccharomyces pompe* TPI gene (Russell (1985) Gene 40125-130).

In the vector, the polynucleotide sequence is operably connected to a suitable promoter sequence. The promoter may be any nucleic acid sequence which shows transcriptional activity in the host cel of choice including mutant, truncated, and hybrid promoters, and may be obtained from genes encoding extra-cellular or intra-cellular polypeptides either homologous or heterologous to the host cell.

Examples of suitable promoters for directing the transcription in a bacterial host cell, are the promoters obtained from the *E. coli* lac operon, *Streptomyces coelicolor* agarase gene (dagA), *Bacillus subtilis* levansucrase gene (sacB), *Bacillus licheniformis* alpha-amylase gene (amyL), *Bacillus stearothermophilus* maltogenic amylase gene (amyM), *Bacillus amyloliquefaciens* alpha-amylase gene (amyQ), and *Bacillus licheniformis* penicillinase gene (penP). Examples of suitable promoters for di-recting the transcription in a filamentous fungal host cel are promoters obtained from the genes for *Aspergillus oryzae* TAKA amylase, *Rhizomucor miehei* aspartic proteinase, *Aspergillus niger* neutral alpha-amylase, and *Aspergillus niger* acid stable alpha-amylase. In a yeast host, useful promoters are the *Saccharomyces cerevisiae* Mal, TPI, ADH, TDH3 or PGK promoters.

The polynucleotide sequence encoding the insulin peptide backbone for use according to the invention also will typically be operably connected to a suitable terminator. In yeast, a suitable terminator is the TPI terminator (Aber et al. (1982) J. Mol. Appl. Genet. 1419-434).

The procedures used to combine the polynucleotide sequence encoding the insulin analogue for use according to the invention, the promoter and the terminator, respectively, and to insert them into a suitable vector containing the information necessary for replication in the selected host, are well known to persons skilled in the art. It will be understood that the vector may be constructed either by first preparing a DNA construct containing the entire DNA sequence encoding the insulin backbones for use according to the invention, and subsequently inserting this fragment into a suitable expression vector, or by sequentially inserting DNA fragments containing genetic information for the individual elements such as the signal and pro-peptide (N-terminal extension of the B-chain), C-peptide, A- and B-chains, followed by ligation.

The vector comprising the polynucleotide sequence encoding the insulin analogue for use according to the invention is introduced into a host cell, so that the vector is maintained as a chromosomal integrant, or as a self-replicating extra-chromosomal vector. The term "host cell" encompasses any progeny of a parent cel that is not identical to the parent cel due to mutations that occur during replication. The host cell may be a unicellular microorganism, e.g. a prokaryote, or a non-unicellular microorganism, e.g. a eukaryote. Useful unicellular cells are bacterial cells such as gram-positive bacteria including, but not limited to, a *Bacillus* cell, a *Streptomyces* cell, or a gram-negative bacteria such as *E. coli* and *Pseudomonas* sp. Eukaryote cells may be mammalian, insect, plant, or fungal cells.

The host cel may in particular be a yeast cell. The yeast organism may be any suitable yeast organism which, on cultivation, secretes the insulin peptide backbone or the precursor hereof into the culture medium. Examples of suitable yeast organisms include strains selected from *Saccharomyces cerevisiae, Saccharomyces kluyveri, Schizosaccharomyces pombe, Saccharomyces uvarum, Kluyveromyces lactis, Hansenula polymorpha, Pichia pastoris, Pichia methanolica, Pichia kluyveri, Yarrowia lipolytica, Candida* sp., *Candida utilis, Candida cacaoi, Geotrichum* sp., and *Geotrichum fermentans*.

The transformation of the yeast cells may for instance be affected by protoplast formation followed by transformation by known methods. The medium used to cultivate the cells may be any conventional medium suitable for growing yeast organisms.

Insulin Analogue Purification

The secreted insulin analogue or precursor hereof may be recovered from the medium by conventional procedures including separating the yeast cells from the medium by centrifugation, by filtration or by catching or adsorbing the insulin analogue or precursor hereof on an ion exchange matrix or on a reverse phase absorption matrix, precipitating the proteinaceous components of the supernatant, or by filtration by means of a salt, e.g. ammonium sulphate, followed by purification by a variety of chromatographic procedures, e.g. ion exchange chromatography, affinity chromatography, etc.

The purification and digestion of the insulin peptide backbones of this invention is carried out as follows:

The single-chain insulin analogue precursor, which may contain an N-terminal extension of the B-chain and a modified C-peptide between the B-chain and the A-chain, is purified and concentrated from the yeast culture supernatant by cation exchange (Kjeldsen et al. (1998) Prot. Expr. Pur. 14 309-316).

The single-chain insulin analogue precursor is matured into two-chain insulin peptide backbone by digestion with lysine-specific immobilised ALP (Kristensen et al. (1997) J. Biol. Chem. 20 12978-12983) or by use of trypsin to cleave off the N-terminal extension of the B-chain, if present, and the C-peptide.

ALP Digestion

The eluate from the cation exchange chromatography step containing the insulin peptide backbone precursor is diluted with water to an ethanol concentration of 15-20%. Sodium glutamate is added to a concentration of 15 mM and pH is adjusted to 9.7 by NaOH. Immobilised ALP (4 gram/L) is added in a proportion of 1:100 (volume:volume) and digestion is allowed to proceed with mild stirring at room temperature overnight.

The digestion reaction is analysed by analytical LC on a Waters Acquity Ultra-Performance Liquid Chromatography system using a C18 column and the molecular weight is confirmed by Matrix-Assisted Laser Desorption Ionisation time-of-flight (MALDI-TOF) mass spectrometry (MS) (Bruker Daltonics Autoflex II TOF/TOF).

The immobilised ALP is removed by filtration using a 0.2 µm filter. The two-chain insulin peptide backbone is purified by reversed phase HPLC (Waters 600 system) on a C18 column using an acetonitrile gradient. The desired insulin is recovered by lyophilisation.

Purity is determined by analytical LC on a Waters Acquity Ultra-Performance Liquid Chromatography system using a C18 column, and the molecular weight is confirmed by MALDI-TOF MS.

Example 1

Prepared by General Procedure (B)
A9E, B3E, B26E, desB30 human insulin (SEQ ID NOS: 3 and 4)

Example 2

Prepared by General Procedure (B)
A9E, B3E, B27E, B28E, desB30 human insulin (SEQ ID NOS: 3 and 5)

Example 3

Prepared by General Procedure (A)
A9E, B3E, B26E human insulin; (SEQ ID NOS:3 and 6)

Example 4

Prepared by General Procedure (A)
A9E, B3E, B27E, B28E human insulin; (SEQ ID NOS: 3 and 7)

Example 5

Prepared by General Procedure (B)
A9D, B3E, B26E, desB30 (SEQ ID NOS: 8 and 4)

Example 6

Prepared by General Procedure (B)
A9E, A21A, B3E, B26E, desB30 (SEQ ID NOS: 9 and 4)
Comparator Compound 1
B3E, B26E, desB30 human insulin;
Comparator Compound 2
B3E, B27E, B28E, desB30 human insulin;
Comparator Compound 3
B28D human insulin (Insulin Aspart)
Comparator Compound 4
A21A, B3E, B26E, desB30 human insulin

Example 7

Insulin Receptor Affinity of Selected Insulin Derivatives of the Invention, Measured on Solubilised Receptors The relative binding affinity of the insulin analogues of the invention for the human insulin receptor (IR) is determined by competition binding in a scintillation proximity assay (SPA) (according to Glendorf T et al. (2008) Biochemistry 47 4743-4751).

In brief, dilution series of a human insulin standard and the insulin analogue to be tested are performed in 96-well Optiplates (Perkin-Elmer Life Sciences) followed by the addition of [125I-A14Y]-human insulin, anti-IR mouse antibody 83-7, solubilised human IR-A (semipurified by wheat germ agglutinin chromatography from baby hamster kidney (BHK) cells overexpressing the IR-A holoreceptor), and SPA beads (Anti-Mouse polyvinyltoluene SPA Beads, GE Healthcare) in binding buffer consisting of 100 mM HEPES (pH 7.8), 100 mM NaCl, 10 mM MgSO4, and 0.025% (v/v) Tween 20. Plates are incubated with gentle shaking for 22-24 h at 22° C., centrifuged at 2000 rpm for 2 minutes and counted on a TopCount NXT (Perkin-Elmer Life Sciences).

Data from the SPA are analysed according to the four-parameter logistic model (Vølund A (1978) Biometrics 34 357-365), and the binding affinities of the analogues calculated relative to that of the human insulin standard measured within the same plate.

Insulin receptor affinities and other in vitro data of selected insulin analogues of the invention are presented in Table 1, below.

TABLE 1

Insulin receptor affinities, IGF-1 receptor affinities and functional lipogenesis potencies of insulins of the invention

| Example No. | hIRA (% rel to HI) Ex 7 | hIRA mem (% rel to HI) Ex 8 | hIGF1R mem (% rel to HI) Ex 8 | Lipogenesis (% rel to HI) Ex 9 |
|---|---|---|---|---|
| 1 | 83.2 | 55.8 | 10.2 | 68.2 |
| 2 | 59.5 | 35.4 | 16.5 | 46.5 |
| 5 | 75.5 | ND | ND | ND |
| 6 | 35.3 | ND | ND | ND |

In conclusion, insulin analogues of the invention have high affinity for the insulin receptor, and they are able to activate the receptor and elicit functional response. Furthermore, relative affinity of the insulin analogues of the invention for IGF-1 receptor is lower compared to affinity for insulin receptor. This represents a potential benefit with regards to the safety of the analogues of the invention in clinical practice as mitogenic response would be lower compared to the metabolic response.

Example 8

Insulin and Insulin-Like Growth Factor-1 Receptor Affinities of Selected Insulin Derivatives of the Invention, Measured on Membrane Associated Receptors Membrane-associated human IR and IGF-1R are purified from BHK cells stably transfected with the pZem219B vector containing either the human IR-A, IR-B or IGF-IR insert. BHK cells are harvested and homogenized in ice-cold buffer (25 mM HEPES pH 7.4, 25 mM CaCl2) and 1 mM MgCl2, 250 mg/L bacitracin, 0.1 mM Pefablock). The homogenates are layered on a 41% (w/v) sucrose cushion and centrifuged for 75 minutes at 95000 g at 4° C. The plasma membranes are collected, diluted 1:5 with buffer (as above) and centrifuged again for 45 minutes at 40000 g at 4° C. The pellets are re-suspended in a minimal volume of buffer and drawn through a needle (size 23) three times before storage at −80° C. until usage.

The relative binding affinity for either of the membrane-associated human IR-A, IR-B or IGF-1R is determined by competition binding in a SPA setup. IR assays are performed in duplicate in 96-well OptiPlates (Perkin-Elmer Life Sciences). Membrane protein is incubated with gentle agitation for 150 minutes at 25° C. with 50 μM [125I-A14Y]-human insulin in a total volume of 200 μL assay buffer (50 mM HEPES, 150 mM NaCl, 5 mM MgSO4, 0.01% Triton X-100, 0.1% (w/v) HSA (Sigma A1887), Complete EDTA-free protease inhibitors), 50 μg of wheat germ agglutinate (WGA)-coated PVT microspheres (GE Heathcare) and increasing concentrations of ligand. Assays are terminated by centrifugation of the plate at 2000 rpm for 2 minutes and bound radioactivity quantified by counting on a TopCount NXT (Perkin-Elmer Life Sciences).

IGF-1R assays are conducted essentially as for the IR binding assays except that membrane-associated IGF-1R and 50 μM [125I-Tyr31]-human IGF-1 were employed. Data from the SPA are analysed according to the four-parameter logistic model (Vølund A (1978) Biometrics 34 357-365), and the binding affinities of the analogues to be tested are calculated relative to that of the human insulin standard measured within the same plate.

IR (A isoform), and IGF-1R binding data of selected insulin analogues of the invention are given in the Table 1 above.

Example 9

Lipogenesis in Rat Adipocytes

As a measure of in vitro potency of the insulin analogues of the invention, lipogenesis can be used.

Primary rat adipocytes are isolated from the epididymale fat pads and incubated with 3H-glucose in buffer containing e.g. 0.1% fat free HSA and either standard (human insulin, HI) or insulin of the invention. The labelled glucose is converted into extractable lipids in a dose dependent way, resulting in full dose response curves. The result is expressed as relative potency (%) with 95% confidence limits of insulin of the invention compared to standard (HI).

Data are given in the Table 1, above.

Example 10

Preparation of Insulin Compositions

Insulin compositions of the present invention may be prepared as aqueous solutions. The aqueous solution is made isotonic, for example, with sodium chloride and/or glycerol. Furthermore, the aqueous medium may contain buffers and preservatives. The pH value of the preparation is adjusted to the desired value and may be between about 3 to about 8.5, between about 3 and about 5, or about 6.5, or about 7.4, or about 7.5, depending on the isoelectric point, pl, of the insulin analogue in question.

Preparation of Zinc-Free Insulin Compositions

Zinc-free insulin analogues were dissolved in aqueous solution, which in the final composition contained between 0.1 mM and 10 mM insulin analogue, 16 mM m-cresol, 16 mM phenol, and appropriate amounts of nicotinamide and glycerol, and the pH was adjusted to the desired value (between 7.0-8.0, measured at room temperature) using 1 N hydrochloric acid/1 N NaOH. Water was added to the final volume and the solution was sterile-filtered through a 0.2 μm filter. The composition was filled into vials (2 ml vials sealed using crimp caps, penfills sealed using crimp caps, or HPLC vials with screw tops).

TABLE 2

Exemplary compositions of insulin preparations

| Composition | Insulin (mM) | Phenol (mM) | m-cresol (mM) | Nicotinamide (mM) | Glycerol % | Glycerol mM | Propylene glycol % | Phosphate (mM) | Tris (mM) | pH | Citrate (mM) |
|---|---|---|---|---|---|---|---|---|---|---|---|
| A | 0.6 | 16 | 16 | 0 | 2.15 | 233 | 0 | 3 | | 7.4 | |
| B | 0.6 | 16 | 16 | 40 | 1.85 | 200 | 0 | 3 | | 7.4 | |
| B1 | 0.6 | 16 | 16 | 40 | 1.5 | 163 | 0 | 3 | | 7.4 | 5 |
| B2 | 0.6 | 16 | 16 | 40 | 1.5 | 163 | 0 | 3 | | 7.4 | 10 |
| B3 | 0.6 | 16 | 16 | 40 | 1.2 | 130 | 0 | 3 | | 7.4 | 15 |
| B4 | 0.6 | 16 | 16 | 40 | 1.2 | 130 | 0 | 3 | | 7.4 | 20 |
| C | 0.6 | 16 | 16 | 170 | 0.95 | 103 | 0 | 3 | | 7.4 | |
| I | 0.6 | 16 | 16 | 40 | 1.7 | 185 | 0 | 3 | | 7.2 | |
| I1 | 0.6 | 16 | 16 | 20 | 1.7 | 185 | 0 | 3 | | 7.4 | 10 |
| L | 0.6 | 16 | 16 | 40 | 0 | 0 | 1.5 | | 7 | 7.4 | |
| M | 0.6 | 16 | 16 | 40 | 1.8 | 195 | 0 | | 7 | 7.4 | |
| M1 | 0.6 | 16 | 16 | 10 | 1.8 | 195 | 0 | 3 | | 7.4 | 10 |
| D | 1.2 | 16 | 16 | 40 | 1.85 | 200 | 0 | 3 | | 7.4 | |
| D1 | 1.2 | 16 | 16 | 40 | 1.5 | 163 | 0 | 3 | | 7.4 | 10 |
| E | 1.8 | 16 | 16 | 40 | 1.85 | 200 | 0 | 3 | | 7.4 | |
| F | 2.4 | 16 | 16 | 40 | 1.85 | 200 | 0 | 3 | | 7.4 | |
| G | 3.0 | 16 | 16 | 40 | 1.85 | 200 | 0 | 3 | | 7.4 | |
| H | 3.0 | 16 | 16 | 40 | 1.85 | 200 | 0 | 3 | | 7.0 | |
| J | 3.0 | 16 | 16 | 0 | 1.8 | 195 | 0 | 3 | | 7.0 | |
| K | 3.0 | 16 | 16 | 0 | 2.1 | 230 | 0 | 3 | | 7.4 | |
| K1 | 3.0 | 16 | 16 | 0 | 2.1 | 230 | 0 | 3 | | 7.4 | 20 |
| O | 3.0 | 19 | 19 | 40 | 1.7 | 185 | 0 | 3 | | 7.2 | |
| P | 3.0 | 19 | 19 | 40 | 1.7 | 185 | 0 | 3 | | 7.6 | |
| Q | 3.0 | 19 | 19 | 40 | 1.7 | 185 | 0 | 3 | | 8.0 | |

Example 11

Self-Association of Insulin Compositions Measured by Small Angle X-Ray Scattering (SAXS)

SAXS data was used to estimate self-association state of the insulin analogues of the invention under different conditions.

Scattering curve of each experiment was described by the average radius of gyration (Rg) and maximal dimension (Dmax).

Furthermore, the relative amounts of monomer, dimer and larger species in the scattering curve was estimated using the fact that a SAXS scattering profile has an intensity contribution from all individual components in a multicomponent mixture. By using intensities (form factors) from each component it is possible to estimate the volume fraction contribution of each component in the mixture. A system of linear equations using the algorithm of nonnegative or unconstrained least-squares is used to minimize the discrepancy between the experimental and calculated scattering curves. Form factors are calculated from crystal structures of a monomer, dimer, hexamer etc. The volume fractions are expressed in percentages (%).

Results obtained from derivatives of the invention and of derivatives of the prior art are shown in Table 3, below.

TABLE 3

SAXS data of derivatives of the invention, and the comparator insulin analogues

| | | SAXS* formulation as described in example 10 | |
|---|---|---|---|
| Example No. | Composition | M | D + >D |
| 1 | A | 100 | 0 |
| 1 | B | 100 | 0 |
| 1 | C | 100 | 0 |
| 1 | I | 99 | 1 |
| 1 | I1 | 100 | 0 |
| 1 | L | 98 | 2 |
| 1 | M | 100 | 0 |
| 1 | M1 | 100 | 0 |
| 1 | D | 100 | 0 |
| 1 | D1 | 97 | 3 |
| 1 | E | 100 | 0 |
| 1 | F | 100 | 0 |
| 1 | G | 100 | 0 |
| 1 | H | 79 | 21 |
| 1 | O | 90 | 10 |
| 1 | P | 100 | 0 |
| 1 | Q | 100 | 0 |
| 1 | B1 | 100 | 0 |
| 1 | B2 | 100 | 0 |
| 1 | B3 | 100 | 0 |
| 1 | B4 | 100 | 0 |
| 2 | A | 100 | 0 |
| 2 | I | 100 | 0 |
| 2 | B | 100 | 0 |
| 2 | L | 100 | 0 |
| 2 | M | 100 | 0 |
| 2 | O | 100 | 0 |
| 2 | P | 100 | 0 |
| 2 | Q | 100 | 0 |
| 5 | B | 98 | 2 |
| 5 | G | 95 | 5 |
| 6 | B | 91 | 9 |
| Comparator 1 | B | 97 | 3 |
| Comparator 1 | B4 | 95 | 5 |
| Comparator 1 | G | 77 | 23 |
| Comparator 1 | H | 4 | 96 |
| Comparator 2 | A | 100 | 0 |
| Comparator 2 | J | 0 | 100 |

TABLE 3-continued

SAXS data of derivatives of the invention,
and the comparator insulin analogues

| Example No. | Composition | SAXS* formulation as described in example 10 | |
|---|---|---|---|
| | | M | D + >D |
| Comparator 2 | K | 87 | 13 |
| Comparator 2 | K1 | 0 | 100 |
| Comparator 3 | A# | 35 | 65 |
| Comparator 3 | B# | 0 | 100 |
| Comparator 3 | A + Zn | 0 | 100 |
| Comparator 4 | A | 86 | 14 |
| Comparator 4 | K | 42 | 58 |
| Comparator 4 | B4 | 87 | 13 |
| Comparator 4 | K1 | 0 | 100 |

*M: Percentage of monomeric species in composition; D: Percentage of dimeric species in composition; >D: Percentage of species larger than dimeric in composition;
phosphate concentration 7 mM instead of 3 mM In conclusion, the insulin analogues of the invention are less self-associated than the comparator compounds according to the SAXS results. This difference is more pronounced at higher concentrations of the insulin analogues of the invention. It will thus be expected that the insulin analogues of the invention will be absorbed more quickly after subcutaneous injection of especially high concentration compositions.

Example 12

Physical Stability Analysis for Insulin Compositions

Compositions (1 ml) of the insulin analogues of the invention as described in example 10 were transferred into 2 ml vials and sealed using crimp caps. The vials were incubated at 30° C. lying down. Every 2 days, the vial was picked by a robotic arm, and a picture of a standing vial was taken with the background light of 10000 lux. The resulting images were analyzed for the presence of particles using a pixel analysis algorithm. The first day when particles were detected is given in the table below.

TABLE 4 physical and chemical stability of insulin analogues
of the invention in clinically relevant compositions

| Example No. | Composition | Physical Stability Lag time (days) | HMWP formation (4 week at 37° C.) |
|---|---|---|---|
| 1 | A | >35 | 0.1 |
| 1 | B | >35 | 0.2 |
| 1 | C | >35 | 0.2 |
| 1 | I | >35 | 0.1 |
| 1 | L | ND | 0.2 |
| 1 | M | ND | 0.4 |
| 1 | D | >35 | 0.3 |
| 1 | E | >35 | 0.8 |
| 1 | F | >35 | 1.3 |
| 1 | G | >35 | 1.9 |
| 1 | H | 30 | 1.6 |
| 1 | O | >35 | 1.6 |
| 1 | P | >35 | 3.8 |
| 1 | Q | >35 | 8.6 |
| 1 | B1 | >35 | 0.1 |
| 1 | B2 | >35 | 0.8 |
| 1 | B3 | >35 | 0.6 |
| 1 | B4 | >35 | 0.1 |
| 2 | A | >35 | 0.1 |
| 2 | I | >36 | 0.1 |
| 2 | B | >40 | 0.1 |
| 2 | L | >40 | 0.1 |
| 2 | M | >40 | 0.1 |
| 2 | O | >36 | 0.7 |
| 2 | P | >36 | 0.6 |
| 2 | Q | >36 | 1.1 |
| 5 | B | >35 | 0.4 |
| 6 | B | >35 | -0.1 |
| 6 | G | 15 | 2.1* |
| Comparator 1 | B | 12 | 1.9 |
| Comparator 1 | B4 | 2 | 1.7* |
| Comparator 1 | G | 2 | 3.5* |
| Comparator 1 | H | 4 | 3.2* |
| Comparator 2 | A | >36 | 0.8 |
| Comparator 2 | J | 24 | 2.4* |
| Comparator 2 | K | 13 | 3.9* |
| Comparator 2 | K1 | 5 | 1.1* |
| Comparator 3 | A# | 5.3 | 1.6* |
| Comparator 3 | B# | 3.3 | 1.8* |
| Comparator 3 | A + Zn | >43 | 0.5 |
| Comparator 4 | A | 14 | 1.6* |
| Comparator 4 | B4 | 4 | 2.9* | phosphate concentration 7 mM instead of 3 mM
ND: Not Determined
*HMWP was determined in supernatants for samples containing particles; particles were not solubilized.

In conclusion, the insulin analogues of the invention have higher physical stability in clinically relevant Zn-free compositions, especially at high insulin concentration.

Example 13

Chemical Stability Analysis for Insulin Compositions
HMWP Content

High molecular weight proteins (HMWP) were separated from the monomeric form of insulin by size-exclusion chromatography using Waters Insulin HMWP column (125 Å, 10 μm, WAT 201549, 7.8×300 mm) with 0.5 ml/min flow of an eluent containing 50% (v/v) isopropanol, 600 mM NaCl, 20 mM NaH2PO4 and UV detection at 215 nm.

Typical injection volume was 5 μl of 600 μM insulin composition.

The results are shown in Table 4, above.

Example 14

Subcutaneous PK/PD Profiles in LYD Pigs

The insulin analogues of the invention may be tested by subcutaneous administration to pigs, e.g. comparing with insulin aspart in the clinical composition (FIASP®) or comparing with similar insulin analogues of the prior art according to this protocol. The analogues may be tested for pharmacokinetic and/or pharmacodynamic parameters.

General Methods Used

During anaesthesia for placement of permanent intravenous catheters, the pigs are examined by ultrasound with and Esaote ultrasound scanner model "MyLabFive" and a linear probe type "LA435 6-18 MHz".

Mid neck between ear and scapula, on the right and left side, an area of 2×2 cm with no underlying muscle and suitable for subcutaneous injection is identified and marked by tattoo.

Feeding Schedule

The pigs are fasted (no breakfast) prior to the experiment.

The pigs are in their normal pens during the entire experiment and they are not anaesthetized. The pigs are fasted until the 5-hour blood sample has been collected, but with free access to water. After the 5-hour blood sample the pigs are fed food and apples.

Subcutaneous Dosing

The Penfill is mounted in a NovoPen Echo® with Novofine 30G 8 mm needle, using a needle reducer with 5 mm depth, is used for each pig. Each pig is dosed 10U-60 microL of compositions containing 600 nmol/ml insulin analog.

The pig is dosed in the subcutis laterally on the right or left side (opposite the catheter) of the neck and the needle is kept in the subcutis for a minimum of 10 seconds after injection to secure deposition of compound.

Treatment of Hypoglycaemia

After subcutaneous dosing, glucose solution should be ready for i.v. injection to prevent hypoglycaemia, i.e. 4-5 syringes (20 mL) are filled with sterile 20% glucose, ready for use. Diagnosis of hypoglycemia is based on clinical symptoms and blood glucose measurements on a glucometer (Glucocard X-meter).

Treatment consists of slow i.v. injection of 50-100 ml 20% glucose (10-20 g glucose). The glucose is given in fractions over 5-10 minutes until effect.

Blood Sampling

The patency of the jugular catheters is checked prior to the experiment with sterile 0.9% NaCl without addition of 10 IU/mL heparin.

Before and after the dosing, blood samples will be taken in the stable from a central venous catheter at the following time points:

Predose (−15, −5), 3, 6, 9, 12, 15, 20, 30, 40, 50, 60, 80, 100, 120, 150, 180, 240, 300 min.

Samples are taken with a flowswitch. 4-5 ml of waste blood is withdrawn and discarded before taking the sample.

Blood samples of 0.8 ml are collected into tubes coated with EDTA for glucose and insulin analysis.

After each blood sample the catheter is flushed with 5 ml of sterile 0.9% NaCl without addition of 10 IU/mL heparin.

The tube is tilted gently a minimum of 10 times to ensure sufficient mixing of blood and anticoagulant (EDTA) and after one minute it is placed on wet ice. The tubes are spun for 10 min at 3000 rpm and $4^1$C within 1 hour after sampling. The samples are stored on wet ice until pipetting.

Aseptic technique is demanded to avoid bacterial growth in the catheter with increased risk of clotting.

Closure of the Catheters after the Experiment

After the last sample has been collected at the days of dosing, a single intravenous treatment with 1 ml per 10 kg Pentrexyl® (1 g of ampicillin dissolved in 10 ml 0.9% NaCl) is administered slowly i.v. via the catheter used for blood sampling. Following this treatment, the catheter is flushed with 10 ml 0.9% NaCl.

The catheters are closed with 0.5 ml of TauroLockHep500 is injected through the membrane as a lock for the catheter.

Analysis of Blood Samples

Plasma glucose: 10 ul of plasma is pipetted into 500 ul of buffer solution for measurements of glucose concentration in plasma in the BIOSEN autoanalyser.

Plasma insulin: 1×50 µl of plasma are pipetted into 0.65 ml Micronic® tubes (ELISA/LOCI/SPA setup) for analysis.

Plasma is stored frozen at −20° C.

PK calculations: Area under the curve (AUC) to infinity and partial AUCs, AUC0-5, AUC0-10, AUC0-15, AUC0-20 and AUC0-30, were calculated by non-compartmental analysis applying the linear up log up calculation method in Phoenix 64 (Certara, US). The ratio between a partial AUC/AUCinf was used as a measure for absorption rate based on the similar iv properties for the insulin analogues in LYD pig.

Figure 2:
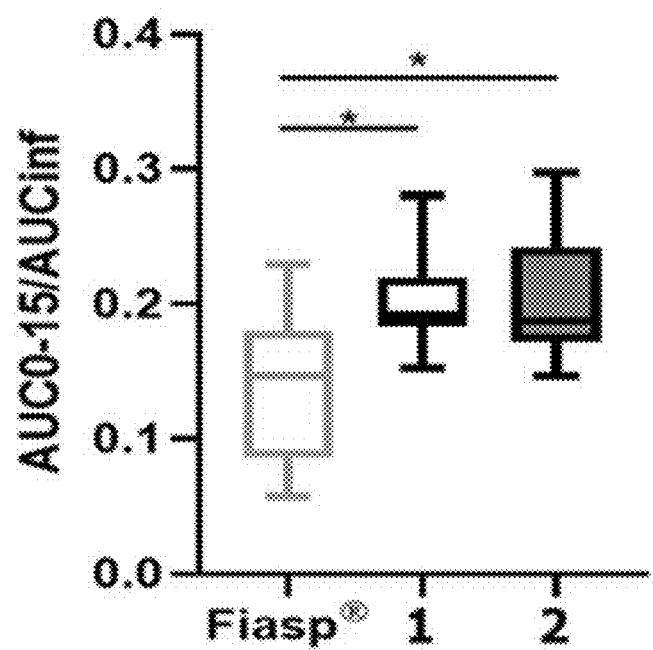
FIG. 2. shows PK profile of insulin analogues of example 1 and example 2 in pharmaceutical composition C of the invention after dosing LYD pigs as compared to Fiasp® (Insulin Aspart)

FIG. 1 and FIG. 2 show that the analogues of the invention are better suited for use in insulin pumps than FIASP® as their onset of action is faster compared to FIASP®; the minimum glucose levels for the insulin analogues of the invention is lower compared to FIASP®. Furthermore, the offset of action is faster for the insulin analogues of the invention when compared to FIASP®, Faster offset of action is beneficial for insulin pumps.

While certain features of the invention have been illustrated and described herein, many modifications, substitutions, changes, and equivalents will now occur to those of ordinary skill in the art. It is, therefore, to be understood that the appended claims are intended to cover all such modifications and changes as fall within the true spirit of the invention.

The invention claimed is:

1. A human insulin analogue, wherein the analogue is selected from the group consisting of:
   A9E, B3E, B26E, desB30;
   A9E, B3E, B27E, B28E, desB30;
   A9D, B3E, B26E, desB30; and
   A9E, A21A, B3E, B26E, desB30; and
   wherein the affinity of the human insulin analogue for an insulin receptor is at least 30% of that of human insulin; and
   wherein the analogue in a pharmaceutical composition is chemically and/or physically stable and particle-free for at least 30 days.

2. The insulin analogue according to claim 1, wherein the analogue is A9E, B3E, B26E, desB30.

3. The insulin analogue according to claim 1, wherein the analogue is A9E, B3E, B27E, B28E, desB30.

4. A pharmaceutical composition comprising an insulin analogue according to claim 1, and one or more pharmaceutically acceptable excipients.

5. The pharmaceutical composition according to claim 4, wherein the insulin analogue is in a concentration of from 0.6 mM to 3 mM.

6. The pharmaceutical composition according to claim 5, wherein the composition is free of zinc.

7. The pharmaceutical composition according to claim 4, further comprising a nicotinic compound.

8. The pharmaceutical composition according to claim 7, wherein the nicotinic compound is nicotinamide.

9. The pharmaceutical composition according to claim 4, wherein the composition is free of a nicotinic compound.

10. The insulin analogue according to claim 1, wherein the insulin analogue is monomeric in a zinc free pharmaceutical composition.

11. A method comprising: treating or alleviating type 1 diabetes and/or type 2 diabetes in a human subject, wherein a therapeutically effective amount of a pharmaceutical composition according to claim 4 is administered to the subject in need of such method.

12. A pharmaceutical composition consisting of a human insulin analogue selected from:
   A9E, B3E, B26E, desB30, and
   A9E, B3E, B27E, B28E, desB30; and
   wherein the insulin analogue is in a concentration of from 0.6 mM to 3 mM;
   wherein the insulin analogue is chemically and/or physically stable;
   wherein the pharmaceutical composition is particle-free for at least 30 days;
   wherein the affinity of the human insulin analogue for an insulin receptor is at least 30% of that of human insulin;
   wherein the composition is zinc free; and
   wherein the composition further contains one or more pharmaceutical excipients and optionally a nicotinic compound.

13. A method comprising: treating or alleviating type 1 diabetes and/or type 2 diabetes in a human subject, wherein a therapeutically effective amount of a pharmaceutical composition according to claim 12 is administered to the subject in need of such method.

14. The pharmaceutical composition according to claim 5, wherein the insulin analogue is in a concentration selected from about 1.2 mM, about 1.8 mM, about 2.4 mM, and about 3.0 mM.

15. The pharmaceutical composition according to claim 12, wherein the insulin analogue is in a concentration selected from about 1.2 mM, about 1.8 mM, about 2.4 mM, and about 3.0 mM.

\* \* \* \* \*

SEQUENCE LISTING

```
<160> NUMBER OF SEQ ID NOS: 9

<210> SEQ ID NO 1
<211> LENGTH: 21
<212> TYPE: PRT
<213> ORGANISM: Artificial Sequence
<220> FEATURE:
<223> OTHER INFORMATION: Synthetic

<400> SEQUENCE: 1

Gly Ile Val Glu Gln Cys Cys Thr Ser Ile Cys Ser Leu Tyr Gln Leu
1               5                   10                  15

Glu Asn Tyr Cys Asn
            20

<210> SEQ ID NO 2
<211> LENGTH: 30
<212> TYPE: PRT
<213> ORGANISM: Artificial Sequence
```

```
<220> FEATURE:
<223> OTHER INFORMATION: Synthetic

<400> SEQUENCE: 2

Phe Val Asn Gln His Leu Cys Gly Ser His Leu Val Glu Ala Leu Tyr
1               5                   10                  15

Leu Val Cys Gly Glu Arg Gly Phe Phe Tyr Thr Pro Lys Thr
            20                  25                  30

<210> SEQ ID NO 3
<211> LENGTH: 21
<212> TYPE: PRT
<213> ORGANISM: Artificial Sequence
<220> FEATURE:
<223> OTHER INFORMATION: Synthetic

<400> SEQUENCE: 3

Gly Ile Val Glu Gln Cys Cys Thr Glu Ile Cys Ser Leu Tyr Gln Leu
1               5                   10                  15

Glu Asn Tyr Cys Asn
            20

<210> SEQ ID NO 4
<211> LENGTH: 29
<212> TYPE: PRT
<213> ORGANISM: Artificial Sequence
<220> FEATURE:
<223> OTHER INFORMATION: Synthetic

<400> SEQUENCE: 4

Phe Val Glu Gln His Leu Cys Gly Ser His Leu Val Glu Ala Leu Tyr
1               5                   10                  15

Leu Val Cys Gly Glu Arg Gly Phe Phe Glu Thr Pro Lys
            20                  25

<210> SEQ ID NO 5
<211> LENGTH: 29
<212> TYPE: PRT
<213> ORGANISM: Artificial Sequence
<220> FEATURE:
<223> OTHER INFORMATION: Synthetic

<400> SEQUENCE: 5

Phe Val Glu Gln His Leu Cys Gly Ser His Leu Val Glu Ala Leu Tyr
1               5                   10                  15

Leu Val Cys Gly Glu Arg Gly Phe Phe Tyr Glu Glu Lys
            20                  25

<210> SEQ ID NO 6
<211> LENGTH: 30
<212> TYPE: PRT
<213> ORGANISM: Artificial Sequence
<220> FEATURE:
<223> OTHER INFORMATION: Synthetic

<400> SEQUENCE: 6

Phe Val Glu Gln His Leu Cys Gly Ser His Leu Val Glu Ala Leu Tyr
1               5                   10                  15

Leu Val Cys Gly Glu Arg Gly Phe Phe Glu Thr Pro Lys Thr
            20                  25                  30

<210> SEQ ID NO 7
<211> LENGTH: 30
<212> TYPE: PRT
```

```
<213> ORGANISM: Artificial Sequence
<220> FEATURE:
<223> OTHER INFORMATION: Synthetic

<400> SEQUENCE: 7

Phe Val Glu Gln His Leu Cys Gly Ser His Leu Val Glu Ala Leu Tyr
1               5                   10                  15

Leu Val Cys Gly Glu Arg Gly Phe Phe Tyr Glu Glu Lys Thr
            20                  25                  30

<210> SEQ ID NO 8
<211> LENGTH: 21
<212> TYPE: PRT
<213> ORGANISM: Artificial Sequence
<220> FEATURE:
<223> OTHER INFORMATION: Synthetic

<400> SEQUENCE: 8

Gly Ile Val Glu Gln Cys Cys Thr Asp Ile Cys Ser Leu Tyr Gln Leu
1               5                   10                  15

Glu Asn Tyr Cys Asn
            20

<210> SEQ ID NO 9
<211> LENGTH: 21
<212> TYPE: PRT
<213> ORGANISM: Artificial Sequence
<220> FEATURE:
<223> OTHER INFORMATION: Synthetic

<400> SEQUENCE: 9

Gly Ile Val Glu Gln Cys Cys Thr Glu Ile Cys Ser Leu Tyr Gln Leu
1               5                   10                  15

Glu Asn Tyr Cys Ala
            20
```